United States Patent
Porter

(10) Patent No.: US 6,247,366 B1
(45) Date of Patent: *Jun. 19, 2001

(54) DESIGN MATURITY ALGORITHM

(76) Inventor: Alexander J. Porter, 2804 Wellington, Kalamazoo, MI (US) 49008

(*) Notice: Subject to any disclaimer, the term of this patent is extended or adjusted under 35 U.S.C. 154(b) by 0 days.

This patent is subject to a terminal disclaimer.

(21) Appl. No.: 09/316,574

(22) Filed: May 21, 1999

Related U.S. Application Data

(63) Continuation-in-part of application No. 08/929,839, filed on Sep. 15, 1997, now Pat. No. 6,035,715.

(51) Int. Cl.[7] ............................ G01M 7/06; G01N 17/02; G01N 17/00
(52) U.S. Cl. ............................ 73/571; 73/663; 73/865.6; 73/432.1
(58) Field of Search .............................. 73/662, 663, 664, 73/665, 666, 667, 668, 865.6, 865.9, 866, 432.1, 672, 571, 573, 574, 788, 794

(56) References Cited

U.S. PATENT DOCUMENTS

| | | | |
|---|---|---|---|
| 2,850,893 | 9/1958 | Barnes, Jr. | 73/71.6 |
| 3,592,041 | 7/1971 | Spencer | 73/7 |
| 3,597,960 | 8/1971 | Otera et al. | 73/12 |
| 3,628,378 | 12/1971 | Regan, Jr. | 73/93 |
| 3,646,807 | 3/1972 | Gray et al. | 73/71.6 |
| 3,664,181 | 5/1972 | Conrad et al. | 73/71.6 |
| 3,712,125 | 1/1973 | Meyer | 73/90 |
| 3,732,380 | 5/1973 | Kimball | 179/100.2 B |
| 3,942,362 | 3/1976 | Keller | 73/88 R |
| 4,069,706 | 1/1978 | Marshall et al. | 73/666 |
| 4,112,776 | 9/1978 | Ouellette et al. | 73/665 |
| 4,181,026 | 1/1980 | Abstein, Jr. et al. | 73/665 |
| 4,181,027 | 1/1980 | Talbott, Jr. | 73/665 |
| 4,181,028 | 1/1980 | Talbott, Jr. | 73/665 |
| 4,232,558 | * 11/1980 | Jon et al. | 73/801 |
| 4,263,809 | 4/1981 | Petersen et al. | 73/789 |
| 4,428,238 | 1/1984 | Tauscher | 73/663 |
| 4,445,381 | 5/1984 | Russenberger | 73/666 |
| 4,489,612 | 12/1984 | Griggs | 73/663 |
| 4,537,077 | 8/1985 | Clark et al. | 73/665 |
| 4,635,764 | 1/1987 | Woyski et al. | 188/268 |
| 4,641,050 | 2/1987 | Emerson et al. | 310/27 |
| 4,658,656 | 4/1987 | Haeg | 73/669 |
| 4,700,148 | 10/1987 | Pauly | 331/154 |
| 4,715,229 | 12/1987 | Butts | 73/663 |
| 4,733,151 | 3/1988 | Butts | 318/645 |
| 4,735,089 | 4/1988 | Baker et al. | 73/663 |
| 4,802,365 | 2/1989 | Sallberg et al. | 73/808 |
| 4,862,737 | 9/1989 | Langer | 73/117 |
| 4,869,111 | 9/1989 | Ohya et al. | 73/811 |

(List continued on next page.)

OTHER PUBLICATIONS

McLinn, James A., "Constant Failure Rate—A Paradigm in Transition?", *Quality and Reliability Engineering International*, vol. 6, pp. 237–241 (1990).

Leonard, Charles T., et al., "How Failure Prediction Methodology Affects Electronic Equipment Design," *Quality and Reliability Engineering International*, vol. 6, pp. 243–249 (1990).

(List continued on next page.)

*Primary Examiner*—Hezron Williams
*Assistant Examiner*—Rose M. Miller

(57) ABSTRACT

An apparatus for optimizing the design of a product or component by subjecting the product or component to multiple stimuli, such as temperature, vibration, pressure, ultraviolet radiation, chemical exposure, humidity, mechanical cycling, and mechanical loading, is described. Also described is a method for determining design maturity, technological limits, technological design maturity, predicted technological design maturity, and system target limits of products, components, and systems, respectively.

35 Claims, 13 Drawing Sheets

U.S. PATENT DOCUMENTS

| | | | |
|---|---|---|---|
| 4,912,980 | 4/1990 | Baughn | 73/663 |
| 4,970,725 * | 11/1990 | McEnroe et al. | 371/15.1 |
| 4,977,342 | 12/1990 | Adams | 310/20 |
| 4,996,881 | 3/1991 | Tauscher et al. | 73/665 |
| 5,038,617 | 8/1991 | Rollet et al. | 73/662 |
| 5,079,955 | 1/1992 | Eberhardt | 73/799 |
| 5,138,884 | 8/1992 | Bonavia | 73/662 |
| 5,154,567 | 10/1992 | Baker et al. | 73/665 |
| 5,156,051 | 10/1992 | Marshall | 73/663 |
| 5,197,333 | 3/1993 | Garcia-Gardea | 73/666 |
| 5,305,645 | 4/1994 | Reifsnider et al. | 73/808 |
| 5,315,882 | 5/1994 | Meyer et al. | 73/862.044 |
| 5,339,677 | 8/1994 | Haug | 73/49.5 |
| 5,339,697 | 8/1994 | Mullin | 73/862.043 |
| 5,343,752 | 9/1994 | Woyski et al. | 73/665 |
| 5,351,545 | 10/1994 | Lucas | 73/663 |
| 5,353,654 | 10/1994 | Lin | 73/865.9 |
| 5,365,788 | 11/1994 | Hobbs | 73/665 |
| 5,375,453 | 12/1994 | Rudd et al. | 73/37 |
| 5,379,645 | 1/1995 | Smart | 73/794 |
| 5,386,728 | 2/1995 | Norton et al. | 73/668 |
| 5,412,991 | 5/1995 | Hobbs | 73/663 |
| 5,425,276 | 6/1995 | Gram et al. | 73/816 |
| 5,431,491 | 7/1995 | Melgaard et al. | 312/232.1 |
| 5,437,191 | 8/1995 | Dripke et al. | 73/816 |
| 5,476,009 | 12/1995 | Dimarogonas | 73/582 |
| 5,487,301 | 1/1996 | Müller et al. | 73/118.1 |
| 5,517,857 | 5/1996 | Hobbs | 73/571 |
| 5,540,109 | 7/1996 | Hobbs | 73/865.6 |
| 5,544,478 | 8/1996 | Shu et al. | 60/39.03 |
| 5,544,528 | 8/1996 | Woyski et al. | 73/665 |
| 5,553,501 | 9/1996 | Gaddis et al. | 73/662 |
| 5,565,618 * | 10/1996 | Hu | 73/1 R |
| 5,574,226 | 11/1996 | Reuther et al. | 73/669 |
| 5,589,637 | 12/1996 | Hobbs | 73/663 |
| 5,594,177 | 1/1997 | Hanse | 73/663 |
| 5,610,344 | 3/1997 | Ueda et al. | 73/865.6 |
| 5,641,912 | 6/1997 | Manahan, Sr. | 73/797 |
| 5,652,386 | 7/1997 | Dimarogonas | 73/582 |
| 5,665,919 | 9/1997 | Woyski et al. | 73/665 |
| 5,675,098 | 10/1997 | Hobbs | 73/865.6 |
| 5,700,951 | 12/1997 | Sagiyama et al. | 73/11.08 |
| 5,715,180 | 2/1998 | Hu | 364/552 |
| 5,744,724 | 4/1998 | Hobbs | 73/665 |
| 5,752,834 | 5/1998 | Ling | 434/58 |
| 5,813,541 | 9/1998 | Mottram | 209/2 |
| 5,836,202 | 11/1998 | Hobbs | 73/665 |
| 5,979,242 * | 11/1999 | Hobbs | 73/663 |
| 6,023,985 * | 2/2000 | Fournier | 73/865.6 |
| 6,035,715 * | 3/2000 | Porter | 73/571 |

OTHER PUBLICATIONS

Wong, Kam L., "What is Wrong With The Existing Reliability Prediction Methods," *Quality and Reliability Engineering International,* vol. 6, pp. 251–257 (1990).

Blanks, Henry S., "Arrhenius And The Temperature Dependence Of Non–Constant Failure Rate," *Quality and Reliability Engineering International,* vol. 6, pp. 259–265 (1990).

Pech, Michael, et al., "The Reliability Physics Approach To Failure Prediction Modelling," *Quality and Reliability Engineering International,* vol. 6, pp. 267–273 (1990).

Pecht, Michael et al., "Temperature Dependence of Microelectronic Device Failures," *Quality and Reliability Engineering International,* vol. 6, pp. 275–284 (1990).

Ganter, William A., "Increasing Importance of Effects of Marginal Parts On Reliability," *Quality and Reliability Engineering International,* vol. 6, pp. 285–288 (1990).

Beasley, Keith, "New Standards For Old," *Quality and Reliability Engineering International,* vol. 6, pp. 295–299 (1990).

Coppola, Anthony, "A Better Method For Verifying Production Reliability," *Quality and Reliability Engineering International,* vol. 6, pp. 295–299 (1990).

Minor, Edward O., "Accelerated Quality Maturity For Avionics," 1996 Proceedings Accelerated Reliability Technology Symposium—Denver, Colorado, Sep. 16–20, 1996, pp. 1–18.

Haibel, Chet., "Design Defect Tracking," 1996 Proceedings—Accelerated Reliability Technology Symposium—Denver, Colorado, Sep. 16–20, 1996, pp. 1–12.

Edson, Larry, "Combining Team Spirit and Statistical Tools With the H.A.L.T. Process," 1996 Proceedings—Accelerated Reliability Technology Symposium—Denver, Colorado, Sep. 16–20, 1996, pp. 1–8.

Stewart, Ph.D., P.E., Bret A., "Fault Coverage and Diagnostic Efficiency Related to Accelerated Life Testing," 1996 Proceedings—Accelerated Reliability Technology Symposium—Denver, Colorado, Sep. 16–20, 1996, pp. 1–5.

Granlund, Kevin, "A Method of Reliability Improvement Using Accelerated Testing Methodologies," 1996 Proceedings—Accelerated Reliability Technology Symposium—Denver, Colorado, Sep. 16–20, 1996, pp. 1–9.

Morelli, Mark L., & Masotti, Robert V., "History of Accelerated Reliability Testing at Otis Elevator Company," 1996 Proceedings—Accelerated Reliability Technology Symposium—Denver, Colorado, Sep. 16–20, 1996, pp. 1–8.

Cooper, Michael R., "Statistical/Numerical Methods for Stress Screen Development," 1996 Proceedings—Accelerated Reliability Technology Symposium—Denver, Colorado, Sep. 16–20, 1996, pp. 1–37.

Blemel, Kenneth G., "Virtual HALT and HASS Planning for Stress Testing From Architecture Selection Through Design," 1996 Proceedings—Accelerated Reliability Technology Symposium—Denver, Colorado, Sep. 16–20, 1996, pp. 1–6.

Moss, Dick, "The Myth of Burn–in," 1996 Proceedings—Accelerated Reliability Technology Symposium—Denver, Colorado, Sep. 16–20, 1996, pp. 1–4.

Hobbs, Gregg K., "Reliability—Past and Present," 1996 Proceedings—Accelerated Reliability Technology Symposium—Denver, Colorado, Sep. 16–20, 1996, pp. 1–5.

O'Connor, Patrick D.T., "Achieving World Class Quality & Reliability: Science or Art?", 1996 Proceedings—Accelerated Reliability Technology Symposium—Denver, Colorado, Sep. 16–20, 1996, pp. 1–4.

Hobbs, Gregg G., "What HALT and HASS Can Do For Your Product," *EE–Evaluation Engineering,* Nov. 1997, pp. 138–142.

Hakim, Edward B., "Microelectronic Reliability/Temperature Independence," *Quality and Reliability Engineering International,* 1991, vol. 7, pp. 215–220.

Smithson, Stephen A., "Effectiveness and Economics," Proceedings of the IES, 1990, pp. 737–742.

Lambert, Ronald G., "Case Histories of Selection Criteria For Random Vibration Screening," *Journal of Environmental Sciences,* Jan./Feb. 1995, pp. 19–25.

* cited by examiner

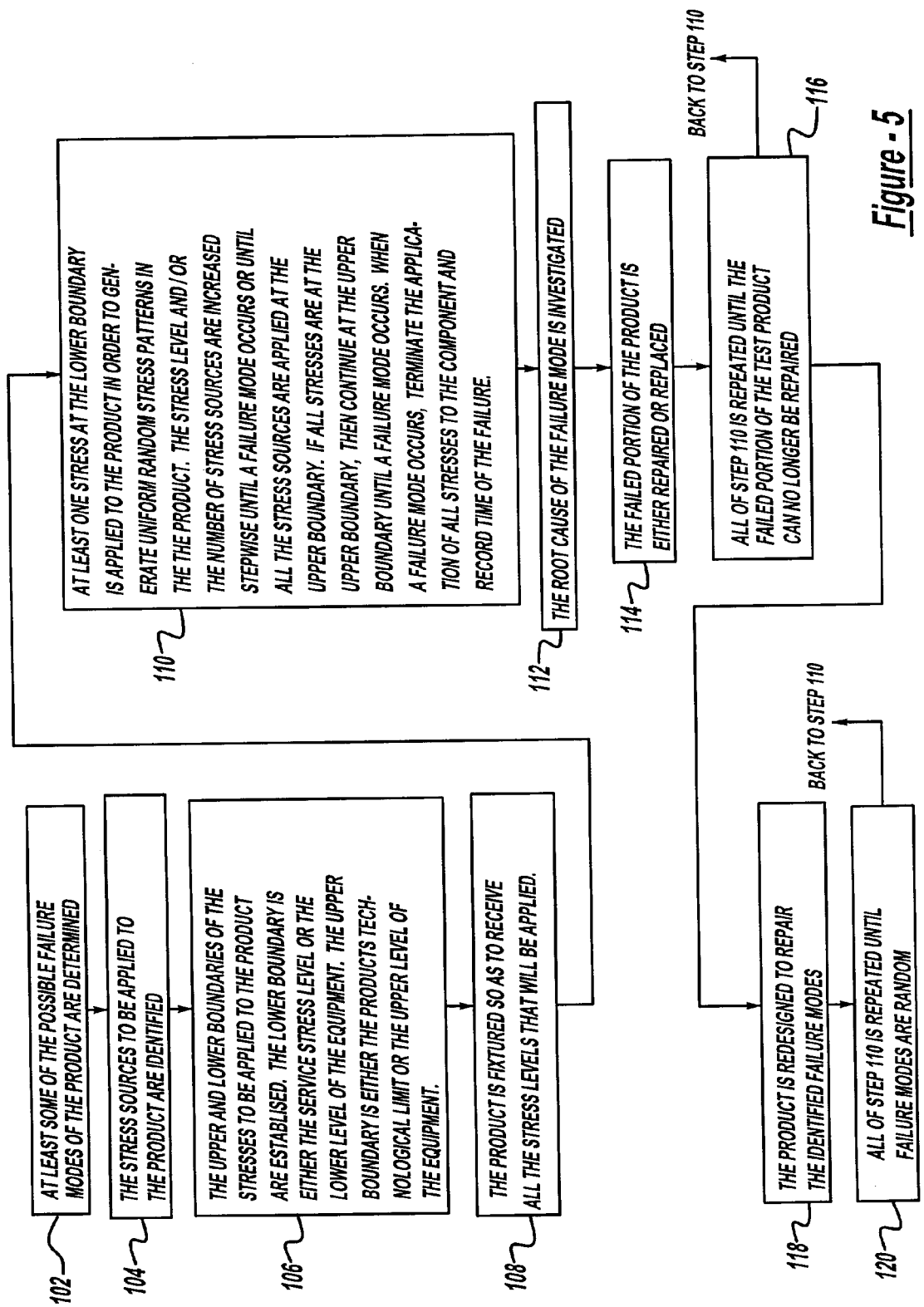

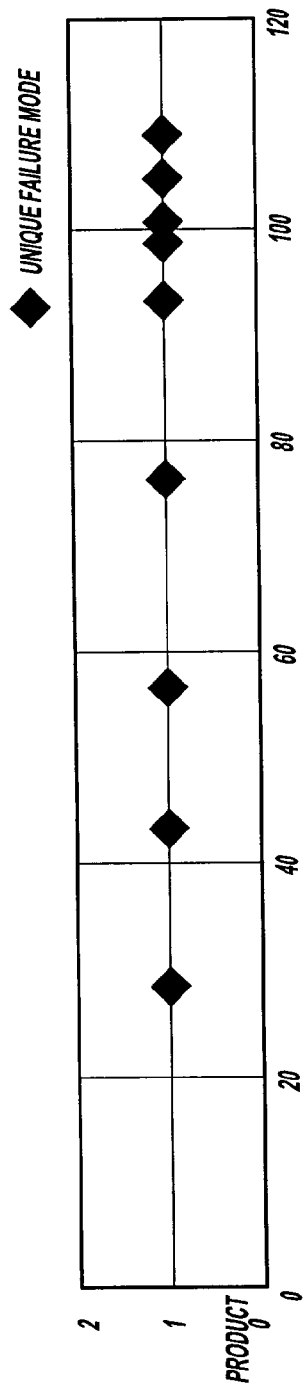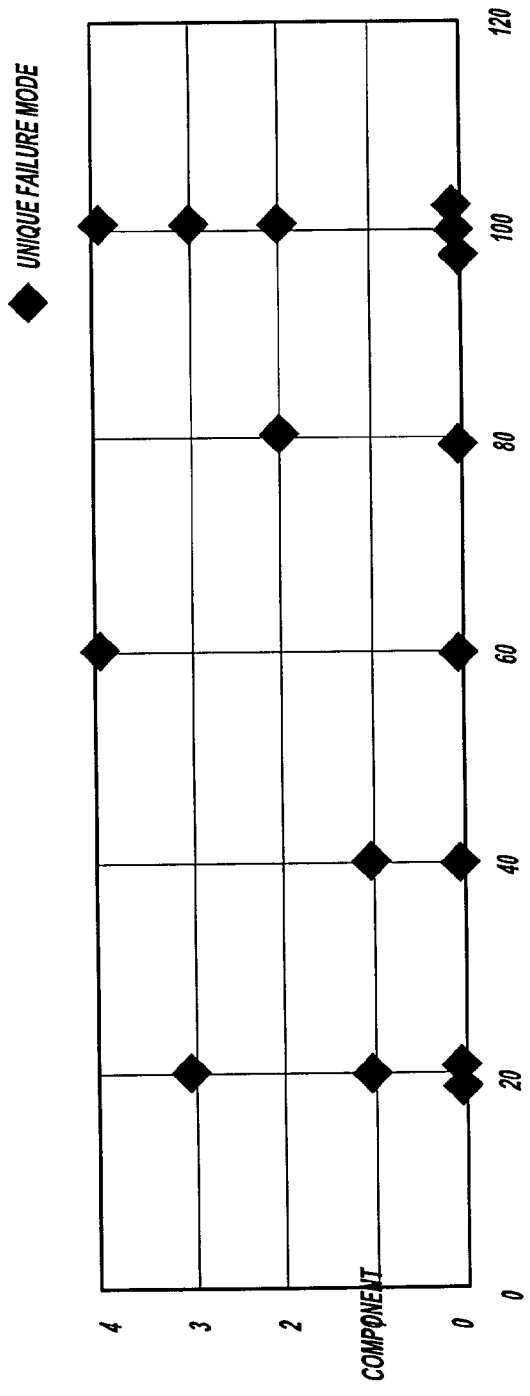

Definitions

| Term | Abreviation | Suffixes | Definition |
|---|---|---|---|
| Accumulated cost of fixing of failure modes below the ith. | ACi | | Accumulated cost of fixing of failure modes below the ith. |
| Cost of fixing a failure mode | C | | Cost of fixing a failure mode |
| The number of components in a system | Component count | | The number of components in a system |
| Number of failure modes in a component | Count | | Number of failure modes in a component. |
| Design maturity | DM | | A measure of the designs maturity based on the potential for improvement by eliminating failure modes. The value reflects a potential improvements in life. A value of 0.1 indicates a potential for a 10 percent gain in life by fixing the first mode. |
| Design maturity benefit ratio | DMBR | | The ratio between the change in potential design maturity and the cost of producing that change. |
| Investment threshold | IT | | The investment willing to be made double life of a product. |
| System | N.A. | | A system is a group of components assembled to perform a function |
| Component | N.A. | | A component is a section of the system that can function independent of the rest of the system. A component is made up of the group of features. |
| Potential design maturity | PDMi | | The design maturity of the component is the fist I failure modes were eliminated. |
| Primary system target limit | PSTL | | The technological limit of the system based on the primary technological design maturity. |
| Primary technological limit | PT | | The cumlative time under the testing scheme below which any failure modes should be fixed so that the product design maturity will be below 0.1. |
| Primary technological design maturity | PTDM | | Design maturity of hte system based on the primary technological limits. |
| Secondary system target limit | SSTL | | The technological limit of the system based on the secondary technological design maturity. |
| Secondary technological limit | ST | | The cumulative time under the testing scheme below which any failure modes should be fixed so that the potential change in design maturity is below 0.1. |
| Secondary technological design maturity | STDM | | Design maturity of the system based on the secondary technological limits. |
| Time to first failure | T1 | | |
| Time to final failure | Tf | | |
| Hard failure | | h | The failure from which the component of system does not recover even when the stress source that caused failure is removed. |
| Calculation with the first T failure removed | | I | Suffix used on calculations to indicate the calculation is based on a subset of the failure modes in which the first i failure modes have been removed. |
| Component number | | n | Component number. |
| Soft failure | | s | A failure for which the component or system will recover after the stress source that caused the failure is removed. |

*Figure - 8*

DESIGN MATURITY ALGORITHM

CROSS-REFERENCE TO RELATED APPLICATION

This application is a continuation-in-part application of U.S. patent application Ser. No. 08/929,839, Sep. 15, 1997 now U.S. Pat. No. 6,035,715 entitled "Method and Apparatus For Optimizing the Design of Products", filed Sep. 15, 1997, pending, the entire specification of which is expressly incorporated herein by reference.

FIELD OF THE INVENTION

The present invention relates to a new and improved apparatus for optimizing the design of products by simultaneously subjecting the products to varying levels of multiple stimuli, and a method for determining the design maturity of the products.

BACKGROUND OF THE INVENTION

One of the major concerns of manufacturers is the discovery of latent defects or flaws which may eventually lead to the failure of a product, component or subcomponent (the terms "product," "component," and "subcomponent," are being used interchangeably throughout the instant application). For this reason, manufacturers have employed various testing procedures that expose a mechanical product, component, or subcomponent to various stresses that would normally be expected to contribute to any number of possible failure modes. Once the failure modes were identified, the manufacturers could then redesign the products in order to reduce or even eliminate the failure modes. Examples of stresses include, without limitation, pressure, ultraviolet radiation, chemical exposure, vibration, temperature (e.g., extreme heat or extreme cold, and rapid changes in temperature), humidity, mechanical cycling (e.g., repeatedly opening and closing a hinged door), and mechanical loading.

Previously, laboratories typically conducted standard testing of mechanical products and components using traditional success based testing. This meant that the goal of the test was to measure the number of products or components that successfully survived a specified number of cycles with a specified stress source level (e.g., vibration, cycle load, temperature, humidity). This testing was generally based on field data and manufacturing/design experience.

Another testing approach was based on the introduction of all the stress sources at service levels to an entire system to provide the final verification test before production. This approach was intended to be a recreation of exact stresses seen on a system during field conditions. For example, an automobile cooling system would receive road vibration, glycol flow, pressure, heat, and ambient conditions just as would be expected to occur during a standard test track durability test.

Another major concern of manufacturers is determining and quantifying the design maturity of their products in order to enable them to make intelligent decisions as to whether certain defects should or should not be addressed. Design maturity is generally defined as a measure of a design's maturity based on the potential for improvement in life span by eliminating failure modes.

Generally, random stresses applied to an immature product design tend to cause the accumulation of stress damage throughout the product at a faster rate as compared to more mature product designs (i.e., product designs that have been redesigned numerous times to eliminate actual and potential failure modes). The faster accumulation of stress damage near the immature product design features tends to result in failures at these particular locations after a relatively short period of time. Continued stress testing causes other less immature features to accumulate stress damage and to eventually also fail. Obviously, a large number of failure modes at a relatively early stage of a product's life span will have negative implications for a manufacturer, such as increased warranty claims and customer dissatisfaction. Manufacturers have resorted to reliability studies to attempt to gather information on how long a particular product or component can be subjected to certain stress levels before failing. However, this does not give the manufacturer any significant information as to precisely what the results and benefits of a successful redesign of that failed product or component would be.

Although redesigns of the particular product design features may eliminate failures, or alternatively, increase the time to failure of those features, there currently is no reliable and quantifiable method for providing the manufacturer with the necessary information to decide whether a redesign of a product design feature will be cost effective, and if so, what will be the benefits of the redesign, for example, in terms of increased feature life span.

Therefore, there is a need for an apparatus which is capable of generating all possible stress patterns in mechanical products and components under varying simultaneous stimuli in order to activate failure modes, and a method for determining and quantifying the design maturity of the mechanical products and components based on the information generated by the activation of the failure modes.

Testing in accordance with the present invention can lead to significant product quality improvements, design cost reductions, production cost reductions, reduced warranty repair expense, increased customer satisfaction, and increased market share.

SUMMARY OF THE INVENTION

General objects of the present invention are to facilitate and enhance testing of products under various conditions, to provide more comprehensive testing and to make testing more efficient by reducing the energy, time, and expense required to undertake testing.

One aspect of the present invention is to allow products to be more comprehensively tested under multiple stimuli including, but not limited to, temperature, vibration, pressure, ultraviolet radiation, chemical exposure, humidity, mechanical cycling, and mechanical loading. In accordance with this aspect of the present invention, the apparatus of the present invention allows products to be tested under varying simultaneous multiple stimuli including, but not limited to, vibration, temperature, pressure, ultraviolet radiation, chemical exposure, humidity, mechanical cycling, and mechanical loading, in order to identify the failure modes of the products.

In accordance with another aspect of the present invention, products are exposed to stimuli that produce uniform random stress patterns in the product.

In accordance with another aspect of the present invention, products are exposed to stimuli that produce six axis uniform random stress patterns in the product.

In accordance with another aspect of the present invention, products may be exposed to varying levels of stimuli. Further, these stimuli may be applied simultaneously to the products. Finally, the level of these simultaneous stimuli may be varied during the course of being applied to the products.

In accordance with another aspect of the present invention, products are tested in order to determine their design maturity measure. The design maturity measure of the products are determined by an algorithm that employs the number of failure modes encountered, and the times that the failure modes occurred (e.g., the time that the first failure mode occurred, the time that the last failure mode occurred, and the times that all other failure modes occurred) as data inputs. The design maturity measure can then be expressed as a design maturity measure percentage by multiplying the design maturity measure by one hundred.

In accordance with another aspect of the present invention, a product's primary and second technological limits are determined.

In accordance with another aspect of the present invention, a product's primary and secondary technological design maturity measures are calculated. The primary and secondary technological design maturity measures can then be expressed as primary and secondary technological design maturity measure percentages by multiplying the primary and secondary technological design maturity measures by one hundred.

In accordance with another aspect of the present invention, a product's predicted primary and secondary technological design maturity measures are calculated. The predicted primary and secondary technological design maturity measures can then be expressed as predicted primary and secondary technological design maturity measure percentages by multiplying the predicted primary and secondary technological design maturity measures by one hundred.

In accordance with another aspect of the present invention, a product's primary and secondary system target limitations are determined.

A more complete appreciation of the present invention and its scope can be obtained from understanding the accompanying drawings, which are briefly summarized below, the followed detailed description of the invention, and the appended claims.

BRIEF DESCRIPTION OF THE DRAWINGS

FIG. 5 is a flow chart of a method for testing a product under different conditions, in accordance with the general teachings of the present invention.

FIG. 6 is a graphical illustration of hypothetical unique failure modes of a product plotted against time, in accordance with one aspect of the present invention.

FIG. 7 is a graphical illustration of hypothetical unique failure modes of the components of a product plotted against time, in accordance with one aspect of the present invention.

FIG. 8 is a series of definitions of terms, abbreviations, and suffixes, in accordance with one aspect of the present invention.

The same reference numerals refer to the same parts throughout the various Figures.

DETAILED DESCRIPTION OF THE INVENTION

Figure 1:
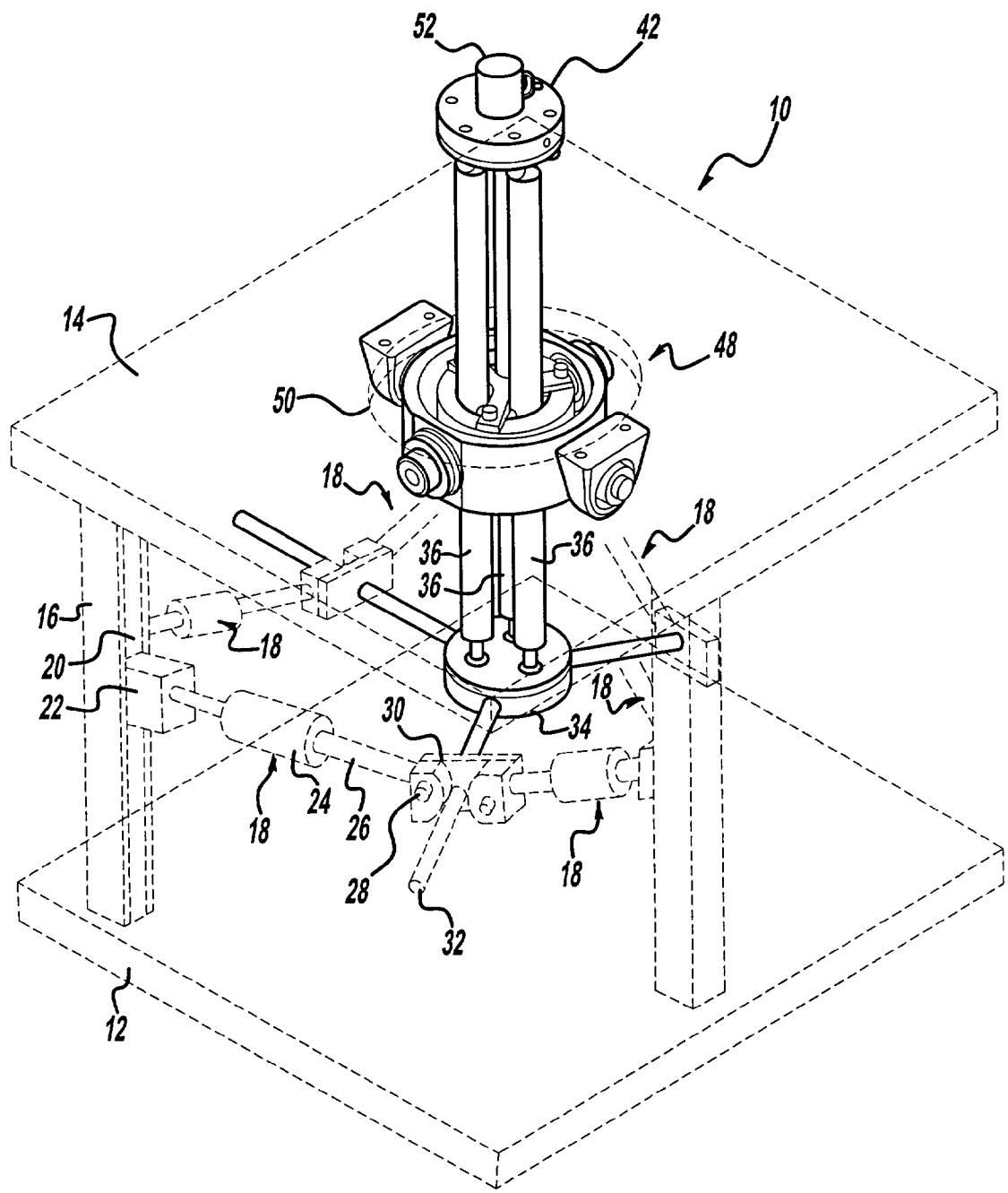
FIG. 1 is a perspective view of an apparatus for testing a product under different conditions, in accordance with one aspect of the present invention.

Generally, mechanical systems typically have resonance frequencies below 200 Hz. Accordingly, a mechanical system (e.g., product, component, subcomponent) may be broadly defined as a system that has at least one mode shape at a frequency below 200 Hz. Conversely, a solid state system typically has a first resonant frequency (also defined as the first mode shape) above 200 Hz.

One of the primary objects of the present invention is to develop a method and apparatus for creating a wide variety of stress patterns, especially six axis uniform random stress patterns, in a product, component, or subcomponent in order to activate the failure modes of that particular product, component, or subcomponent. A six axis uniform random stress is generally defined as the stress history at a point having uniform random distribution with the stress being comprised of tension and compression stress in three orthogonal axes and torsion stress about the same three orthogonal axes. Six axis uniform random stress patterns are generally defined as six axis uniform random stress at all points on a product such that the stress history of the six axis uniform random stress at each point forms a time history of non-repeating stress patterns. All possible stress patterns have an equal probability at any time.

Although the primary focus of the present invention is mechanical products, components, and subcomponents, it should be appreciated that the present invention can be practiced on other types of products, components, and subcomponents, such as, but not limited to brackets, clamps, fasteners, decorative attachments, and many other products which do not meet the definition of a mechanical system.

In a preferred embodiment, it has been found that the use of six axis uniform random actuation at one or more mounting locations of a product will produce six axis uniform random stress patterns in the product. These six axis uniform random stress patterns will identify failure modes previously uncovered with other testing methodologies. Furthermore, the simultaneous introduction of other stimuli (at varying levels), such as temperature, vibration, pressure, ultraviolet radiation, chemical exposure, humidity, mechanical cycling, and mechanical loading, will identify other failure modes associated with the product.

The use of less than six axis actuation (either of input directly to mounting locations of the product or through the use of a rigid table that is activated to six axis motion by some member) will result in less than all of the possible stress patterns being developed and included in the random stress time history of the product. The lack of these stress patterns in the time history of the product has the potential of failing to activate a failure mode in the design of the product. Additionally, the use of three, four, five, or six axis motion in which one or more of the axis motions are dependent on one or more of the other axes will result in certain stress patterns being generated repeatedly with the loss of other stress patterns. Both of these situations have the potential of failing to produce the stress patterns necessary to activate a failure mode which will therefore go undetected until these stress patterns are encountered in field service.

Figure 2:
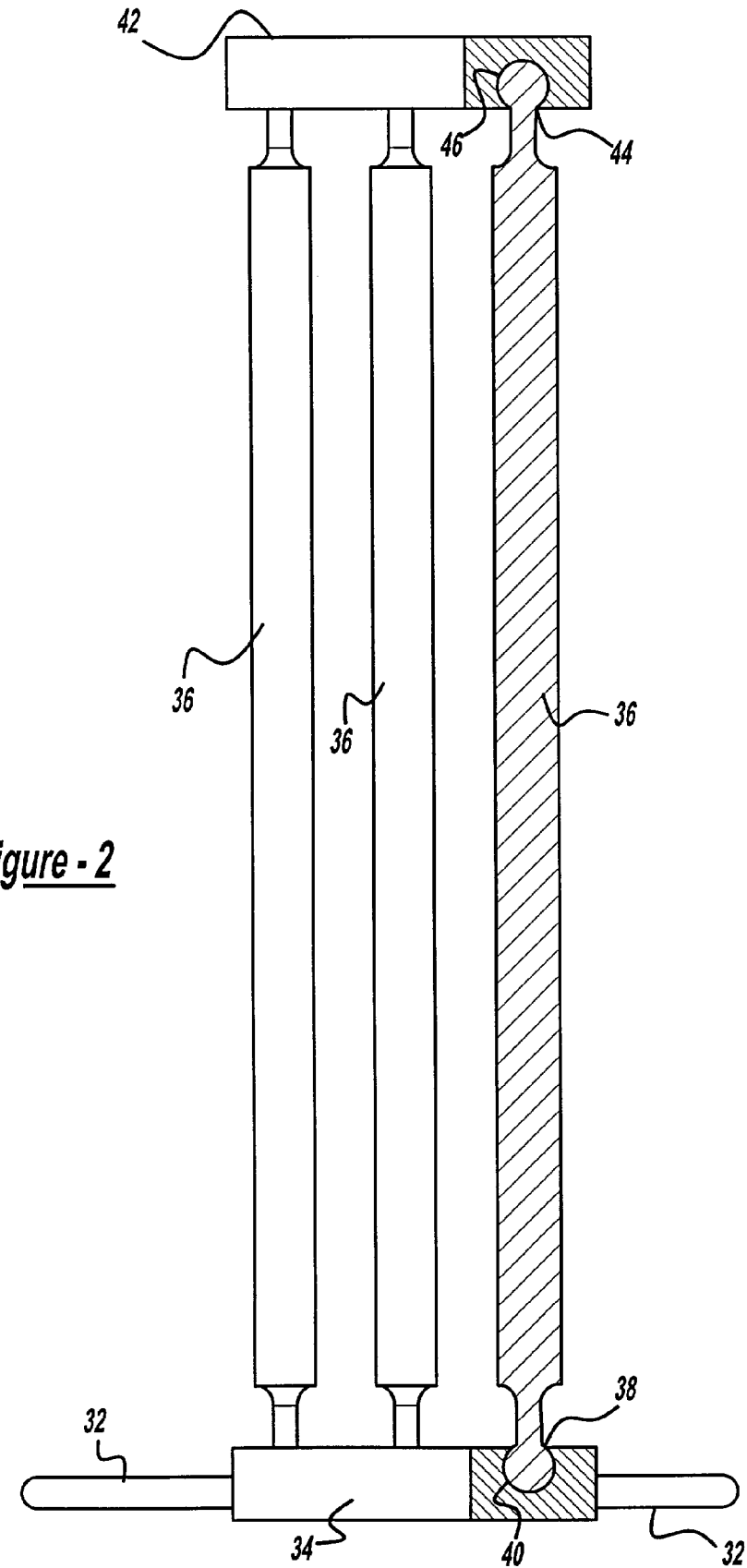
FIG. 2 is a partial cross-sectional view of a portion of the apparatus shown in FIG. 1, in accordance with one aspect of the present invention.
Figure 3:
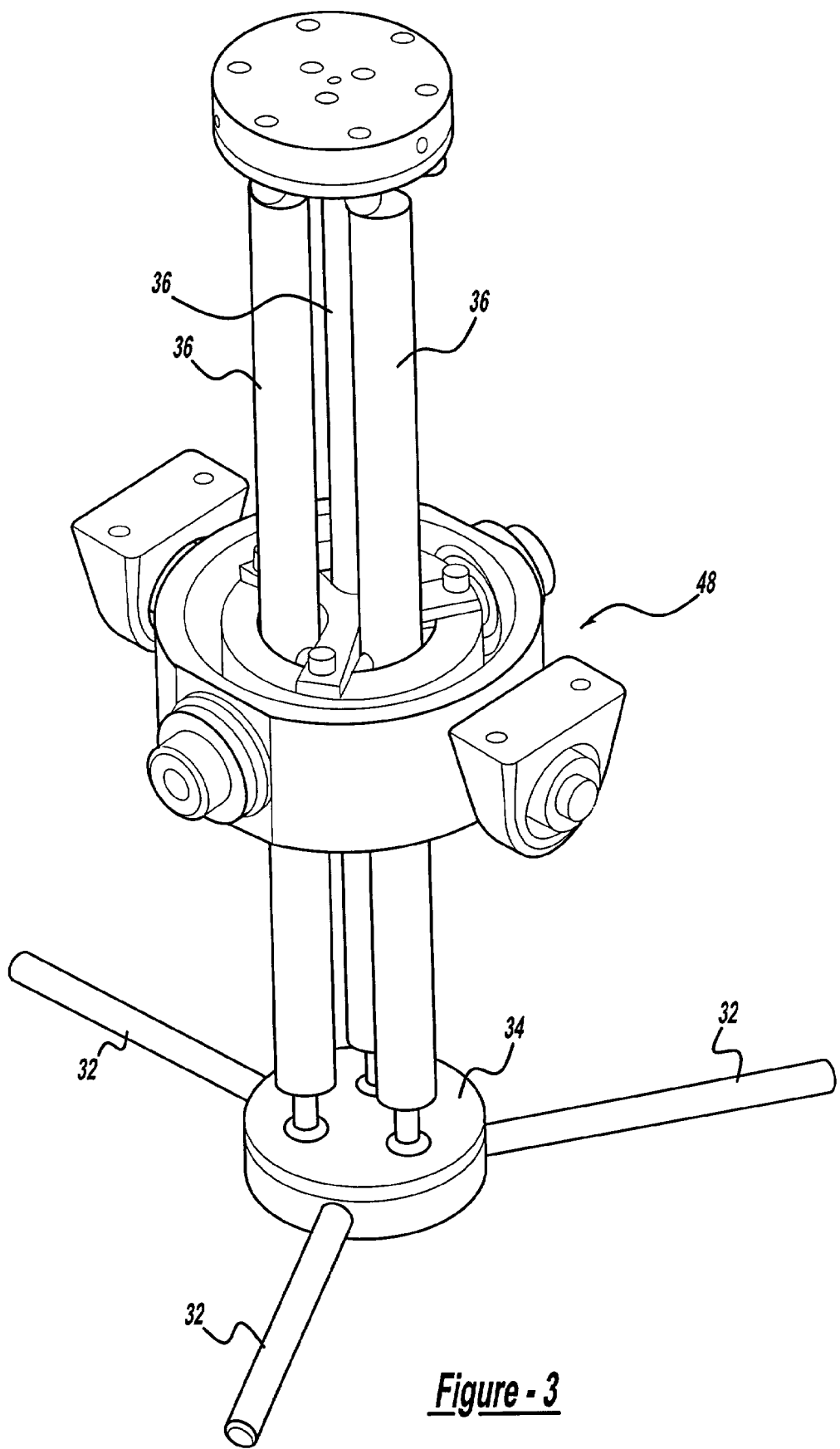
FIG. 3 is an perspective view of a portion of the apparatus shown in FIG. 1, in accordance with one aspect of the present invention.

Referring now to FIGS. 1–3, there is shown a perspective view of an apparatus 10 for testing a product under different conditions in accordance with one aspect of the present invention. The frame of the apparatus 10 consists primarily of a base 12, a planar member 14, and a plurality of support members 16 that rigidly attach the base 12 to the planar member 14. Additionally, a pair of spaced and opposed endwalls and sidewalls (not shown) could be employed in order to form an enclosure around the frame.

The base 12 can be constructed of any suitable material provided that it is substantially flat, durable and of sufficient mass to prevent unintended movement of the apparatus 10 during routine operation. Similarly, the planar member 14 can be constructed of any suitable material. The planar member 14 should preferably be substantially flat in order to provide a flush surface for the top edges of the plurality of support members 16. Although only three support members are shown in the drawing, it should be noted that the use of less than or more than three support members is also envisioned.

The plurality of support members 16 serve two primary purposes. First, the plurality of support members 16 rigidly connect the base 12 to the planar member 14. Second, the plurality of support members 16 provide a member to attach a plurality of actuators 18 (some actuators may not be fully depicted due to the orientation of FIG. 1).

The actuators 18, also referred to as force imparting members, may be operated either pneumatically, hydraulically, by a combination of both pneumatic and hydraulic power, or any other force imparting mechanism. Although six actuators are shown in the drawing, it should be noted that the use of less than six actuators is also envisioned. The plurality of actuators 18 may be attached to the plurality of support members 16 in any number of suitable ways. However, it is preferable for the plurality of actuators 18 to be slidably attached to the plurality of support members 16 in order to allow the plurality of actuators 18 a certain degree of freedom of movement. For example, the plurality of support members 16 can be adapted to contain a recess 20 extending vertically along its length. The plurality of actuators 18 could be fitted with an attachment member 22 which could contain an appendage which is loosely received within the recess 20.

Additionally, the attachment member 22 could then be rigidly fastened to the plurality of support members 16 to keep the plurality of actuators 18 in place.

If six actuators 18 are being used, they should preferably be arranged in pairs, each pair being set about 120 degrees apart from the other pair. Each actuator 18 is simply comprised of a cylinder 24 (some cylinders may not be fully depicted due to the orientation of the figures) acting in cooperation with a piston 26 (some pistons may not be fully depicted due to the orientation of the figures) in order to produce force and torque upon a point of rotation. The pressure to each actuator 18 is preferably cycled between maximum extend pressure and maximum retract pressure in a linear "saw-tooth" manner. The frequency for each actuator 18 will be slightly different. This difference in frequency will cause an interference pattern of the cycling as the actuators 18 come in and out of phase with each other. It is this difference in the frequencies of the actuators which creates a six axis uniform random stress in the product. By way of a non-limiting example, the six pneumatic actuators 18 may be operated at frequencies of 1.8 Hz, 1.9 Hz, 2.0 Hz, 2.1 Hz, 2.2 Hz, 2.3 Hz, and 2.4 Hz, respectively. Therefore, as the actuators 18 come in and out of phase with one another, the frequency content in the center will go from about 2 Hz to infinity. It should be noted that other frequencies may be used for the individual actuators 18 in order to produce an even lower frequency.

Preferably, the piston portion of each actuator 18 is rotatably fastened to a universal joint 28, which is in turn rotatably fastened to a slide 30, which is in turn rotatably attached to an attachment member 32 that extends outwardly from a central hub 34. It should be noted that there are a plurality of attachment members 32, which generally correspond in number to the number of slides 30. It should also be noted that each pair of universal joints 28 is attached to its own individual slide 30. The attachment member 32 can comprise any number of suitable members or devices such as rods, bolts, nuts and lock washers, metallurgical attachment (welding), hyper-elastic or semi-elastic restraint, mechanical spring, or ball and socket.

As the actuators 18 are actuated, they produce a force upon the universal joint 28, which is then transferred from the universal joint 28 to the slide 30, which is then transferred from the slide 30 to the attachment member 32, which is then transferred from the attachment member 32 to the central hub 34, which at that point may generate a torque. It should be noted that whether a torque is generated about the central hub 34 will depend upon which actuators are being actuated and in what sequence with respect to one another.

The central hub 34 is rotatably engaged to at least one, and preferably a plurality of (e.g., three), force transfer members 36. The primary purpose of the force transfer members 36 is to transfer the force and torque originally created by the plurality of actuators 18 at the central hub 34 to the product itself. Any number of suitable devices can be employed as the force transfer members 36, such as, but not limited to, a plurality of preferably elongated and rigid rod members. Referring specifically to FIGS. 2 and 3, it should be noted that each of the bottom surfaces of the force transfer members 36 has a ball member 38 extending therefrom. The ball member 38 cooperates with a corresponding socket 40 disposed on the top surface of the central hub 34 permitting the force transfer members 36 to rotate freely thereabout.

The mounting of the product to the force transfer members 36 is accomplished through a mounting hub 42, which is spaced and opposed from the central hub 34. Referring specifically to FIGS. 2 and 3, it should be noted that each of the top surfaces of the force transfer members 36 has a ball member 44 extending therefrom. The ball member 44 cooperates with a corresponding socket 46 disposed on the bottom surface of the mounting hub 42 permitting the force transfer members 36 to rotate freely thereabout.

The terms "mounting" or "fixturing" are broadly defined to include any member for allowing a stimuli to be applied to the product. Therefore, mounting and fixturing do not necessarily require the product to be fastened rigidly in any one given fixed position by a mechanical device of some sort. For example, the product could merely be placed upon a surface and be subjected to vibration or heat stimuli.

Mounting hub 42 can comprise any number of suitable members or devices such as slots, depressions, wells, chambers, clamps, bolts, screws, hooks, fasteners, adhesives, straps, glue, welding (metallurgical attachment), intermediate spacer block or fixture, suction (vacuum), electromagnetic, and in some cases in which the other mounting locations are securely mounted, the attachment can be simply being in contact or periodic contact. Preferably, if a product has a number of mounting locations (e.g., an automobile dashboard) it should have an apparatus in accordance with the present invention mounted to each mounting location in order to maximize the benefits of the testing. Alternatively, an apparatus in accordance with the present invention could also be mounted to the product at a non-mounting location.

The force transfer members 36 extends upwardly from the central hub 34 until they pass through a device, such as a gimbal member or assembly 48, for allowing the force transfer members 36 to move longitudinally and in all three axes. The gimbal assembly 48 is mounted to the planar member 14 in proximity to an area defining an aperture 50 located in the planar member 14. In a preferred embodiment, the gimbal assembly 48 is comprised of an outer race mounted through an appropriate member so that it can rotate freely perpendicular to its main centerline; an inner race mounted through bearings to the outer race such that it can rotate freely perpendicular to its main centerline and perpendicular to the outer race's axis of rotation; an inner linear bearing (e.g., member for allowing a rod to move linearly through the gimbal assembly 48) which supports the force transfer members 36. The gimbal assembly 48 is nominally mounted at the midpoint of the force transfer members 36. In an alternative embodiment, the gimbal assembly 48 may be adjustable in order to move upwardly or downwardly along the force transfer members 36.

Once passing through the gimbal assembly 48, the force transfer members 36 continue to extend upwardly until they terminate at the mounting hub 42. The mounting hub 42 is shown here securing a workpiece 52, such as a cup. However, many other types of products and components are envisioned to be tested, such as, but not limited to, automotive components, aircraft components, marine components, consumer products, and construction materials.

The force transfer members 36, which are independent of one another, are free to rotate about three axes while having no freedom of motion in any linear direction relative to the central hub 34. This configuration allows for better transmission of rotational degrees of freedom in the horizontal plane. By way of a non-limiting example, when the central hub 34 tilts about an axis, one of the force transfer members 36 will be pulled downwardly while another one of the force transfer members 36 will be pushed upwardly causing the mounting hub 42 to tilt. By way of a non-limiting example, this configuration can increase the rotational degrees of freedom translated from a few degrees to about 30 degrees.

Figure 4A:
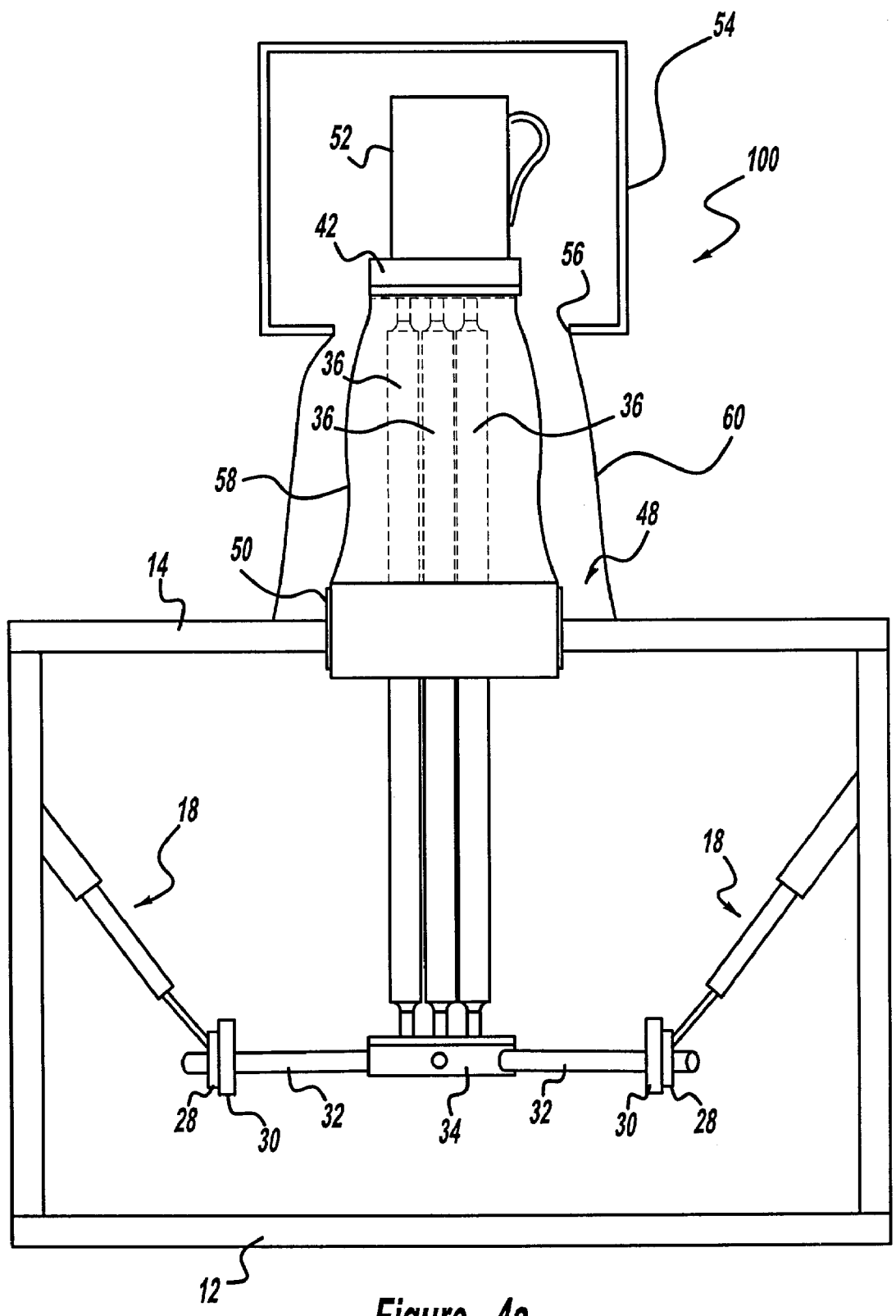
FIGS. 4A and 4B are perspective views of apparatuses for testing a product under different conditions, in accordance with another aspect of the present invention.
Figure 4B:
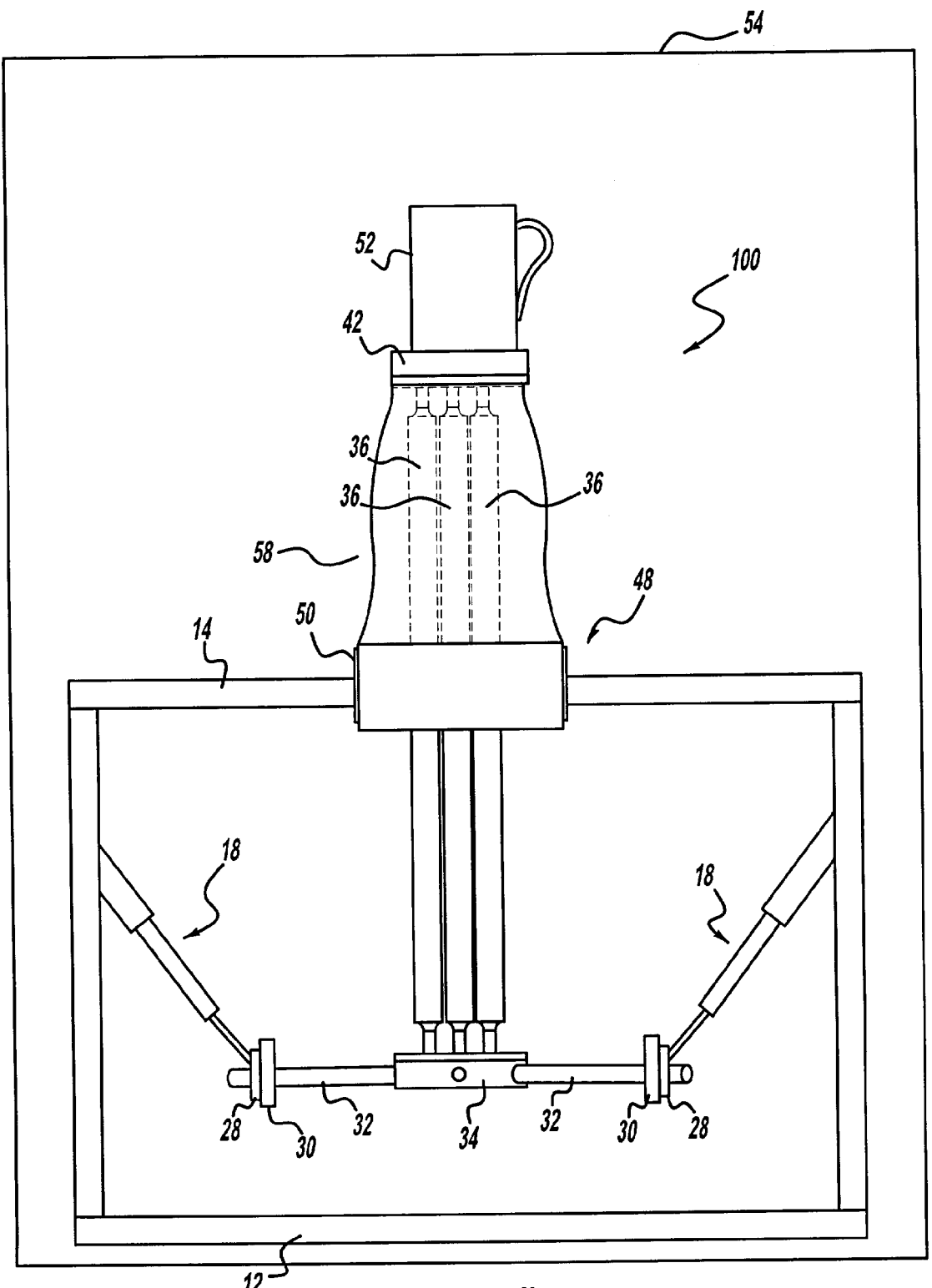

Referring to FIGS. 4A and 4B, two alternative embodiments of the present invention are shown.

Referring specifically to FIG. 4A, the mounting hub 42 and the fixtured product 52 are contained within a housing such as an environmental (e.g., thermal) chamber 54, or other suitable structure. The chamber 54 preferably includes an area defining an aperture 56 for receiving the force transfer members 36 and the mounting hub 42.

The chamber 54 preferably does not interfere with the action or movement of the force transfer members 36 or the mounting hub 42 during the normal operation of the alternative apparatus 100. Accordingly, the chamber 54 is preferably isolated from the action of the force transfer members 36 and the mounting hub 42. By way of a non-limiting example, the chamber 54 may be secured to a wall, a boom, or to the top surface of the planar member 14.

The chamber 54 is preferably sealable so as to be able to carefully control the introduction and evacuation of stimuli into and out of the chamber 54, as well as controlling the level of stimuli being applied to the product inside the chamber 54. In order to seal the chamber 54 from the outside environment, an optional bellows 58 and diaphragm 60 configuration may be provided. The bellows 58 is secured to the lower portion or surface of the mounting hub 42 and the upper portion or surface of the planar member 14 (e.g., in proximity to the gimbal assembly 48). The diaphragm 60 is secured to lower portion of the chamber 54 (e.g., in proximity to the aperture 56) and the upper portion or surface of the planar member 14 (e.g., in proximity to the gimbal assembly 48), thus enveloping the bellows 58. In this instance, it would be preferable to house the actuators 18, as well as the universal joints 28, slides 30, attachment members 32, and the central hub 34 in a sealable enclosure so as not to interfere with the environmental conditions within the chamber 54.

Referring specifically to FIG. 4B, the apparatus 100 is contained entirely within chamber 54, thus negating the need for the aperture 56 and the diaphragm 60.

Although not specifically illustrated in the figures, the apparatus of the present invention can also comprise means or assemblies for actuating the plurality of force imparting members (e.g., pneumatic actuators), means or assemblies for subjecting the product to vibration, means or assemblies for subjecting the product to a temperature, means or assemblies for subjecting the product to pressure, means or assemblies for subjecting the product to ultraviolet radiation, means or assemblies for subjecting the product to chemical exposure, means or assemblies for subjecting the product to humidity, means or assemblies for subjecting the product to mechanical cycling, means or assemblies for subjecting the product to mechanical loading, means or assemblies for controlling the amount of vibration that the product is subjected to by the apparatus, means or assemblies for controlling the level of temperature that the product is subjected to by the apparatus, means or assemblies for controlling the level of pressure that the product is subjected to by the apparatus, means or assemblies for controlling the level of ultraviolet radiation that the product is subjected to by the apparatus, means or assemblies for controlling the level of chemical exposure that the product is subjected to by the apparatus, means or assemblies for controlling the level of humidity that the product is subjected to by the apparatus, means or assemblies for controlling the amount of mechanical cycling that the product is subjected to by the apparatus, and means or assemblies for controlling the amount of mechanical loading that the product is subjected to by the apparatus.

The apparatus of the present invention is capable of producing a frequency range from about 2 Hz to infinity. However, in practice the damping properties of the joints and materials of the product will limit the upper frequency that can be achieved. Additionally, the apparatus can be placed in any suitable chamber that is preferably capable of producing a thermal range between at least −60 degrees C. to at least 177 degrees C., a controlled temperature ramp rate of at least 5 degrees C./minute and humidity between 5% to 95% relative humidity.

An example of a method of testing a product under different conditions in order to identify all of its possible failure modes would comprise the following general methodology and is also illustrated in the flow chart depicted in FIG. 5.

Referring to FIG. 5, at step 102, at least some of the possible failure modes of the product are determined. Possible failure modes are generally determined by past experience (e.g., warranty claims, field data, previous testing), computer modeling, production experience, and materials failure analysis. It is noteworthy that not all the failure modes may be identified. Nevertheless, they may ultimately appear as a result of the application of stresses Referring to FIG. 5, at step 104, the stress sources to be applied to the product are identified. The possible stress sources to be applied are determined in the same manner as in step 102 in that all failure modes identified in step 102 are used and all stress sources that contribute to those failure modes are listed. However, knowledge of failure modes does not necessarily identify the root cause of an individual root stress. For example, a plastic break may require optical inspection, such as scanning electron microscopy, to determine fracture type before the underlying stress causing the fracture may be determined.

Referring to FIG. 5, at step 106, the upper and lower boundaries of the stresses to be applied to the product are established. The lower stress boundary is either the service stress level or the lower level of the equipment being used. The upper stress boundary is either the product technological limit or the upper level of the equipment being used. The lower stress boundary is determined by: (1) service stress levels for the product which may be determined by past experience, expectations, or computer modeling or (2) the lower controllable level of the equipment, with service stress levels being preferred over the lower controllable level of the equipment. The upper stress boundary is determined by: (1) the product technological limit (which may not be known) which is the destruct limit of the product's constitutive materials; or (2) the lower controllable level of the equipment, with the product technological limit being preferred over the upper controllable level of the equipment.

Referring to FIG. 5, at step 108, the product is fixtured so as to receive all the stress levels and sources that will be applied. For example, humidity will be applied by delivering humid air to the product by placing the product in a chamber available from any number of sources such as Thermatron (Grand Rapids, Mich.). With respect to temperature, there are two basic stress sources: (1) actual temperature and (2) temperature ramp rate. Accordingly, the maximum upper temperature, the minimum lower temperature, and the temperature ramp rate all need to be determined. Dwell time is minimized such that it allows the product to reach the temperature of the chamber. With respect to vibration, preferably each mounting location or point of the product is connected or mounted to an apparatus in accordance with the present invention. The six axis apparatus in accordance with the present invention may either be in the chamber itself or extending through a diaphragm or sleeve into the chamber. With respect to ultraviolet radiation, a device such as carbon arc lamp can be placed in the chamber itself. With respect to chemical exposure or attack, this can be accomplished in several ways. First, the product can be exposed prior to actual testing. Additionally, real time exposure may be achieved by spraying the chemical on the product while in the chamber. The chemical spray may be applied periodically or continuously. It may be important to have the spray dry out. The chemical stress level can be increased by either increasing the chemical spray rate or increasing the concentration of the chemical spray. With respect to mechanical loading, a pneumatic cylinder is used most of the time. However, dead weights and solenoids may also be used. Both the loading as well as the time for each cycle can be varied. Finally, pressure (such as air pressure)can be applied. In each case, there is a need to provide a member to control and adjust the levels of the various stresses.

Referring to FIG. 5, at step 110, the stress application loop begins. Preferably, at least one stress at the lower boundary is applied to the product in order to generate uniform random stress patterns in the product. However, it should be noted that stress may be applied at any point in the continuum ranging from the lower to the upper boundary. The stress level and/or the number of stress sources are increased stepwise until a failure mode occurs or until all the stress sources are applied at the upper boundary. If all stress sources are at the upper boundary, then continue applying the stress sources at the upper boundary until a failure mode occurs. When a failure mode occurs, terminate the application of all stresses to the product, and record the time of the failure mode.

Referring to FIG. 5, at step 112, the root cause of the failure mode is investigated. This investigation or analysis is also referred to as a failure analysis. First, visual inspection is carried out to determine which feature of the product or system has failed. This includes documentation of the failure that may include written records, photographs or videotape. Second, microscopic inspection is performed if a failure feature has been created. Fractology involves: (a) initial failure evaluation of the fracture face to identify the fracture type. The possible fracture types include fatigue, rupture, chemical attack, overload, torsion, tensile, bending, elongation, and distortion. Documentation of the fracture face is produced which may be written records, photographs or sketches. Third, if no failure feature has been created, then the product is inspected to determine whether the assembly was incorrect, the material was incorrect, or if the production was incorrect. This includes documentation that may include written records, photographs or videotape. Fourth, a stress source determination is carried out. At the stress levels at which testing stopped, apply one stress at a time, starting with the one that most likely caused the failure based on the investigation of the failed product. If no single stress source is found to reproduce the failure, apply a combination of stresses. If no combination of stresses recreates the specific failure mode before different failure modes are created, then the failure mode is random and therefore, the design is optimized. If a failure feature was created and can not be thoroughly understood by microscopic inspection, then further failure analysis is required which requires that the product that failed be removed from further testing. Further failure analysis may include: a scanning electron microscope, chemical analysis to determine chemical composition as well as to detect contaminants, infrared spectroscopy to determine chemical composition as well as to detect contaminants, dye penetration to detect cracks, magnetic flux, x-ray, ultrasound, and finite element analysis.

Referring to FIG. 5, at step 114, the failed portion of the product is either repaired or replaced.

Referring to FIG. 5, at step 116, all of step 110 is repeated until the failed portion of the test product can no longer be repaired.

Referring to FIG. 5, at step 118, the product is redesigned to repair the identified failure modes. In doing so, the following are considered: the time to failure, the number of failure modes, and whether the failure modes were repeatable or random. This is one way of determining whether the product design has been optimized.

Referring to FIG. 5, at step 120, all of step 110 is repeated until the failure modes are random. The failure modes are tracked to determine whether they have been corrected. However, this method does not generate a statistical reliability number.

These steps can be repeated or altered to alternatively or simultaneously include various levels of temperature, vibration, pressure, ultraviolet radiation, chemical exposure, humidity, mechanical cycling, and mechanical loading, depending on the product to be tested.

Figure 5A:
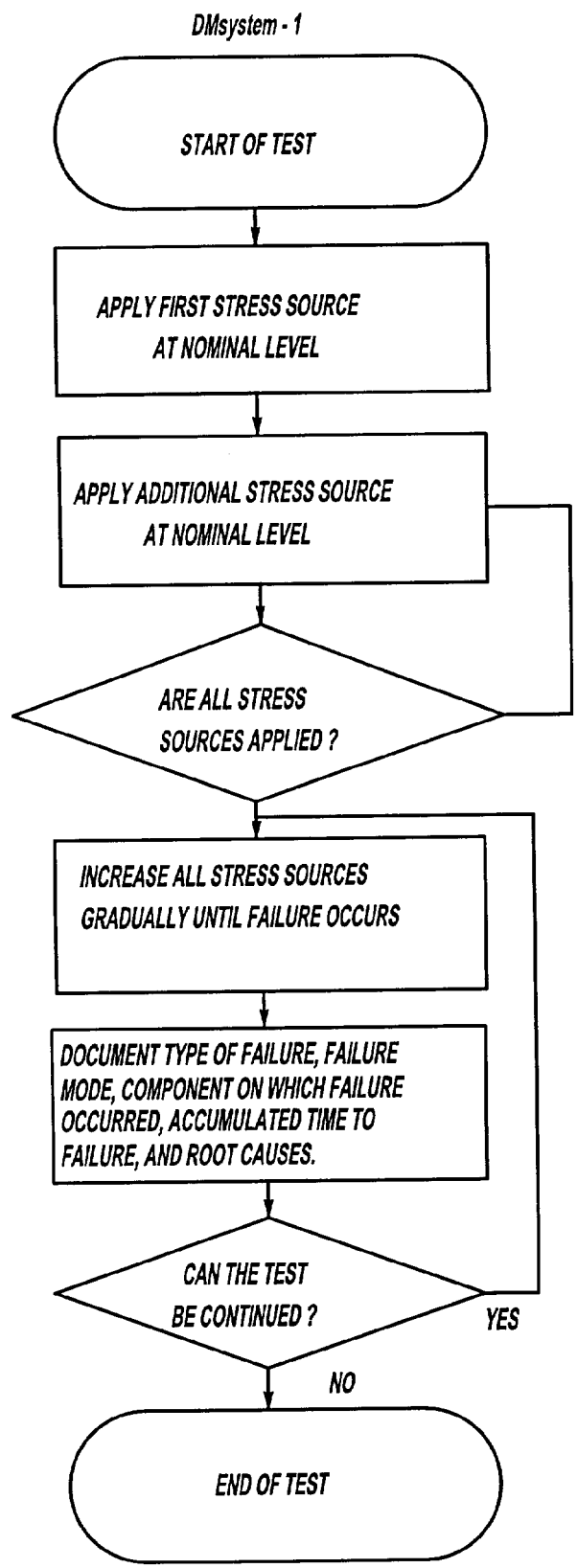
FIG. 5A is a highly simplified flow chart of a method for testing a product under different conditions, in accordance with the general teachings of the present invention.

A highly simplified flow chart of the above described testing procedure is illustrated in FIG. 5A.

An example of a method of testing a product under different conditions in order to identify all of its possible failure modes, is presented below:

EXAMPLE

An automotive cup holder made of a rigid plastic, having a mechanism for storing and deploying the cup holder receptacles, and two cup holder receptacles is chosen as the product to be tested. As defined in step 102, some of the potential failure modes are identified. These are cracking of plastic at mounting boss, sticking of storing mechanism re-engineering the cup holder useless, and assembly clips cracking due to excessive interference. As defined in step 104, all of the stress sources that can produce damage in the part are identified. These are temperature (hot and cold), temperature ramp rate, cycle rate on the storing mechanism, cycle rate on cup insertion (drop), cup load, storing mechanism load, chemical attack from petroleum lubricant, non-petroleum lubricant beverages (coffee, carbonated soda), UV light, and forces at mounting locations (three translations, 3 rotations). As defined in step 106, the upper and lower boundaries of each stress source is established. These are −40 degrees C. to 177 degrees C., a temperature ramp rate of 15 degrees C./minute, 1 storing mechanism/minute to 10 storing mechanism/minute, 1 cup drop/minute to 10 cup drops/minute, ½ lb to 50 lb. cup load, ¼ lb. to 15 lbs. storing mechanism load, no petroleum lubricant to lubricated with SAE 20, no non-petroleum lubricant to lubricated with lithium grease, no beverage to 12 oz. of coffee (regular) poured over component or 12 oz. of cola (regular) poured over component, UV light from one 200 watt UV lamp, 10 lb. peak force and 10 in.-lb. peak torque at each of four mounting locations to 100 lb. peak force and 100 in.-lb. peak torque at each of four mounting locations. As defined in step 108, the four mounting locations are each bolted to one six-axis actuator apparatus, in accordance with general teachings of the present invention. A pneumatic cylinder is positioned to apply the load to the storing mechanism. Two pneumatic cylinders are fitted with mock cups and positioned to apply load to the cup holder receptacles when they are in the open position. The setup is placed in a chamber with heating and cooling controls. Controls are placed on the pneumatic cylinders to create the desired cycle rates. A UV lamp is placed in the chamber. Samples of the lubricants and beverages are prepared. As defined in step 110, the temperature cycle is applied by cycling the temperature from room temperature to 177 degrees C., to −40 degrees C. and back to room temperature. This applies three of the stress stimuli to the product. Then while continuing to apply the thermal cycle, the mounting location energy is applied at all four mounting location at the lowest energy setting listed above. This stress condition is continued for one thermal cycle. While all of the above stimuli are applied at present levels, the mechanical cycling is started with loads and rates at the lowest setting listed above. This stress condition is continued for one thermal cycle. All of the mechanical loading (cycling and mounting points) are raised ¼ of the way to full load. This stress condition is continued for one thermal cycle. All of the mechanical loading (cycling and mounting points) are raised an additional ¼ of the way to full load. This stress condition is continued for one thermal cycle. All of the mechanical loading (cycling and mounting points) are raised an additional ¼ of the way to full load. This stress condition is continued for one thermal cycle. At this point with ¾ of the mechanical loading applied, the first failure mode occurs. This triggers step 112. The initial visual inspection indicates that a plastic tab in the storing mechanism latch has cracked. Optical inspection reveals that the crack originated due to a flaw (cavity) that then fatigued under loading. No further inspection is needed. The crack is documented and repaired (step 114). Step 110 is continued with full mechanical loading for one thermal cycle. The UV light is turned on with all other stress sources at previous levels and another thermal cycle is conducted. A second failure mode occurs. This triggers step 112 for the second time. The initial visual inspection indicates that the edge of one of the cup holder receptacles had cracked. Optical inspection indicates that the lip of the receptacle fatigued. The part on the component is replaced and the mechanical loading of the cup insertion only is applied at previous levels (one stress source) to verify which stress source caused the failure. This stress source does not re-create the failure. The mechanical loading of the cup insertion and the mounting locations is applied at previous levels (two stress source combination) and the failure mode is reproduced. The conclusion is that the mounting location force randomly moves the cup holder so the lip of the cup holder is struck by the simulated cup as it is being inserted. The failure mode is documented and the component is either repaired or replaced (step 114). At this point all stress sources are at the maximum level. Thermal cycles are continued with all stress levels at there previous levels until a failure occurs. A failure occurs after 6 additional thermal cycles. This triggers step 112 for the third time. The initial visual inspection indicates that the hinge of the storing mechanism has worked out of its seat. Optical inspection reveals that there is no failure feature, the parts have simply become separated. Stepping in the stress at the previous levels determines that the mechanical loading of the storing mechanism at higher temperatures (when the plastic was most elastic) caused the hinge to work out of its seat. Step 110 is continued, but no other failure modes can be generated. The third failure mode continues to repeat. Step 118 is conducted to redesign the failed areas. The correction steps are noted and the time to failure and failure modes are complied. Step 110 (per step 120) is repeated. Stresses are added in and raised to maximum levels without failure. Failure finally occurs after 10 thermal cycles at maximum stress (note that this is a significant increase in time to failure). Step 112 reveals that the failure is a crack in the middle of the bottom of the left cut holder. Efforts to reproduce this failure are unsuccessful, in the process two other failure modes occur which can not be reproduced. Random failure modes have been achieved. The part appears to be optimized.

For the following discussion of other aspects of the present invention, reference is made to the definitions of terms, abbreviations, and suffixes disclosed in FIG. 8.

Based on the failure mode data generated during the previously described testing methodology, it is possible to determine and quantify the product's design maturity to generate a design maturity measure. The design maturity measure is preferably expressed in terms of percentage so as to provide a manufacturer with a percent increase in the product or component life span when one or more failure modes are eliminated. It should be noted that the design maturity measure algorithm to be described herein can be used in conjunction with any stress test procedure or methodology that is capable of generating at least two unique failure modes in the product or component. As noted, at least two failure modes are needed to be generated in order to calculate the product's design maturity measure. Accordingly, the maximum number of design maturity measures that can be calculated is always the total number of failure modes encountered minus one. The design maturity measure of a product is calculated by the following algorithm:

$$[((X-Y)/(N-1))/Y] = \text{Design Maturity Measure}$$

wherein X is the elapsed time period until a final unique failure mode was encountered, or any other unique failure mode was encountered other than an initial unique failure mode, during the stress test procedure or any portion thereof;

wherein Y is the elapsed time period until the initial unique failure mode was encountered, or any other unique failure mode was encountered other than the final unique failure mode, during the stress test procedure or any portion thereof; and N is the total number of unique failure modes encountered during the stress test procedure or any portion thereof.

The term "time" refers to any unit of time such as second, minutes, hours, days, and so forth.

The term "initial" refers to the absolute first failure mode encountered. For example, if three failure modes, A, B, and C, were encountered, failure mode A would be considered the initial failure mode.

The term "final" refers to the absolute last failure mode encountered. For example, if three failure modes, A, B, and C, were encountered, failure mode C would be considered the final failure mode.

The phrase "stress test procedure" refers to any method or procedure that results in at least two unique failure modes being generated in a product or component. It is not necessary to run the stress test procedure to the product's or component's technological limit, e.g., the stress test procedure can be administered for any period of time up to, including, or even exceeding the product's or component's technological limit.

It should by noted that because the time units cancel out when the algorithm is calculated, the resulting number is unitless. The design maturity percentage is then simply calculated by multiplying the design maturity measure by 100 to give a percentage.

The following hypothetical illustrations will demonstrate the benefits of the design maturity measure algorithm of the present invention.

In the first hypothetical situation, a product has a first failure mode at 1 hour, a second failure mode at 2 hours, and a third and final failure mode at 9 hours. With respect to determining what the design maturity measure would be if the first failure mode was fixed and eliminated, this data would be incorporated into the algorithm as follows: [((9−1)/(3−1))/1] or [(8/2)/1] or 4. Thus, the products design maturity measure, or DM measure, or DMM, would be expressed by the number 4. The design maturity measure percentage, or DM measure percentage, or DMM percentage, or DMMP, would be calculated as follows: [(4)100] or 400%. This percentage represents the estimated or approximate benefits of fixing and eliminating the first failure mode. In this case, a DM measure of 4 represents a 400% increase in the product's life span if the first failure mode is fixed and eliminated. Presumably, if a manufacturer can increase a product's life span by 400% by simply and inexpensively fixing and eliminating the first failure mode, it would appear to make economic sense to do so in order to reduce potential warranty claims.

In the second hypothetical situation, a product has a first failure mode at 1 hour, a second failure mode at 1.5 hours, and a third and final failure mode at 2 hours. This data would be incorporated into the algorithm as follows: [((2−1)/(3−1))/1] or [(1/2)/1] or 0.5. Thus, the product's DM measure percentage would be 50% (i.e., [(0.5)100]), thus representing a 50% increase in the product's life span if the first failure mode is fixed. Although this hypothetical is not as clear cut as the first hypothetical, if the manufacturer could increase the product's life span by 50% by simply and inexpensively fixing and eliminating the first failure mode, it would also appear to make economic sense to do so in order to reduce potential warranty claims. However, if the first failure mode is difficult and expensive to fix and eliminate, the manufacturer may elect to decline to do so.

In the third hypothetical situation, a product has a first failure mode at 10 hours, a second failure mode at 10.5 hours, and a third and final failure mode at 11 hours. This data would be incorporated into the algorithm as follows: [((11−10)/(3−1))/10] or [(1/2)/10] or 0.05. Thus, the product's DM measure percentage would be 5% (i.e., [(0.05) 100]), thus representing a 5% increase in the product's life span if the first failure mode is fixed and eliminated. This hypothetical is as clear cut as the first hypothetical; however, a completely opposite result will probably occur. If the manufacturer could increase the product's life span by only 5% even by simply and inexpensively fixing a first failure mode, it would appear to make very little economic sense to do so. Furthermore, if the first failure mode is difficult and expensive to fix and eliminate, it would make even less economic sense for the manufacturer to fix it from a purely economical viewpoint.

Although, the above discussion has focused on the benefits of fixing and eliminating the product's first failure mode, it should be noted that the design maturity measure algorithm of the present invention can be employed to determine the benefits of eliminating any particular product failure mode that occurs anytime during the stress test procedure continuum.

To illustrate the benefits of the design maturity measure algorithm, as applied to the second failure mode of the product, consider the previous three hypothetical situations.

In the first hypothetical, the product had a first failure mode at 1 hour, a second failure mode at 2 hours, and a third and final failure mode at 9 hours. This data would be incorporated into the algorithm as follows: [((9−2)/(2−1))/2] or [(7/1)/2] or a DM measure of 3.5. Note that N=2 in this case because only the last two failure modes are used in these calculations. Thus, the product's DM measure percentage would be calculated as follows: [(3.5)100] or 350% (this presupposes that the first failure mode had been previously fixed and eliminated), thus representing a 350% increase in the product's life span if the second failure mode is fixed and eliminated. Compare this to 400% product life span increase accomplished by fixing and eliminating the first failure mode. Clearly, a potential 350% life span increase is highly significant, and accordingly, the manufacturer would probably be inclined to fix and eliminate the second failure mode, in addition to the first failure mode.

In the second hypothetical, the product had a first failure mode at 1 hour, a second failure mode at 1.5 hours, and a third and final failure mode at 2 hours. This data would be incorporated into the algorithm as follows: [((2−1.5)/(2−1))/1.5] or [(0.5/1)/1.5] or a DM measure of 0.33. Note that N=2 in this case because only the last two failure modes are used in these calculations. Thus, the product's DM measure percentage would be calculated as follows: [(0.33)100] or 33% (this presupposes that the first failure mode had been previously fixed and eliminated), thus representing a 33% increase in the product's life span if the second failure mode is fixed and eliminated. However, a potential 33% life span increase is moderately insignificant, and accordingly, the manufacturer would probably be disinclined to fix and eliminate the second failure mode.

In the third hypothetical, the product had a first failure mode at 10 hours, a second failure mode at 10.5 hours, and a third and final failure mode at 11 hours. This data would be incorporated into the algorithm as follows: [((11−10.5)/(2−1))/10.5] or [(0.5/1)/10.5] or a DM measure of 0.05. Note that N=2 in this case because only the last two failure modes are used. Thus, the product's DM measure percentage would be calculated as follows: [(0.05)100] or 5% (this presupposes that the first failure mode had been previously fixed and eliminated), thus representing a 5% increase in the product's life span if the second failure mode is fixed and eliminated. However, a potential 5% life span increase is rather insignificant, and accordingly, the manufacturer would most probably be disinclined to fix and eliminate the second failure mode.

Referring to FIG. 6, a chart of hypothetical unique failure modes of a product is plotted against time. Ideally, the failure modes occur far to the right side of the chart, indicating a long time to failure. However, in this case, the failure modes occur in a fairly linear progression. The first failure mode occurs at around 30 minutes, the second failure at around 40 minutes, the third failure mode occurs at around 55 minutes, the fourth failure mode occurs at around 80 minutes, and the remaining failure modes are clustered at around 100 minutes. If the first failure mode is eliminated, the life span of the product will increase modestly. If both the first and second failure modes are eliminated, the life span of the product will increase still further. If the first, second, third, and fourth failure modes are eliminated, the life span of the product will increase dramatically. Conversely, eliminating the failure modes clustered around 100 minutes will not significantly increase the life span of the product as it has presumably reached its technological limit.

Additionally, the design maturity measure algorithm of the present invention can be used to determine the design maturity of individual components or features of a product, as opposed to the product as a whole. This especially helpful in the context of products that have numerous components, wherein it is difficult to determine which component's failure modes are the most problematic based solely on a design maturity determination of the product as a whole.

Referring to FIG. 7, a chart of hypothetical unique failure modes are plotted by product as a whole and the product's individual components versus time to the particular failure modes. The bottom most plot depicts the total distribution of unique failure modes for the product as a whole. However, the chart also illustrates the distribution of failure modes for each of the four components of the product. In this case, the manufacturer should focus on eliminating the first failure modes of components 1 and 3 as their first failure modes occur after a short period of testing. In this instance, fixing and eliminating the first failure modes of components 1 and 3 will probably result in significantly increased component life span. However, the manufacturer will probably also want to focus on fixing and eliminating the second failure mode of component 1, as this occurs quickly after the first failure mode. The manufacturer should focus less on component 2 as it's first failure mode occurs after a considerable amount of testing has elapsed, most likely occurring near the component's technological limit. In this instance, fixing and eliminating the first failure mode of component 2 will probably not result in significantly increased component life span. Falling somewhere in between these two extremes is the case of component 4, which has it's first failure mode after those of components 1 and 3 but before that of component 2. Accordingly, the manufacturer is faced with the decision of whether it is economically feasible to fix and eliminate the first failure mode. The design maturity measure algorithm of the present invention allows the manufacturer to determine and quantify the benefits of fixing and eliminating any product or component failure mode.

To illustrate the benefits of the design maturity measure algorithm, as applied to the components, consider the following hypothetical situations.

In the first hypothetical situation, component A of a product has a first failure mode at 1 hour, a second failure mode at 2 hours, and a third and final failure mode at 11 hours. This data would be incorporated into the algorithm as follows: [((11−1)/(3−1))/1] or [(10/2)/1] or a DM measure of 5. Thus, component A's DM measure percentage of 500% (i.e., [(5)100]) would represent a 500% increase in component A's life span if the first failure mode is fixed. Thus, if the manufacturer could increase component A's life span by 500% by simply and inexpensively fixing and eliminating the first failure mode, it would appear to make economic sense to do so in order to reduce warranty claims. Even if the elimination of the first failure mode was expensive, the manufacturer still might be inclined to fix and repair it if it significantly reduced or eliminated the number of corresponding warranty claims associated with that component.

In the second hypothetical situation, component B of the same product has a first failure mode at 8 hours, a second failure mode at 8.5 hours, and a third and final failure mode at 9 hours. This data would be incorporated into the algorithm as follows: [((9−8)/(3−1))/8] or [(1/2)/8] or a DM measure of 0.06. Thus, component B's DM measure percentage of 6% (i.e., [(0.06)100]) would represent a 6% increase in component B's life span if the first failure mode is fixed and eliminated. Here, it may not make economic sense for the manufacturer to fix and eliminate the first failure mode of component B as it only results in a modest 6% life span increase.

In the third hypothetical situation, component C of the same product has a first failure mode at 3 hours, a second failure mode at 4 hours, and a third and final failure mode at 5 hours. This data would be incorporated into the algorithm as follows: [((5−3)/(3−1))/3] or [(2/2)/3] or a DM measure of 0.33. Thus, component C's DM measure percentage of 33% (i.e., [(0.33)100]) would represent a 33% increase in component C's life span if the first failure mode is fixed and eliminated. This hypothetical is not as clear cut as the first two hypothetical situations; however, if the manufacturer could increase component C's life span by 33% by simply and inexpensively fixing and eliminating the first failure mode, it would appear to make economic sense to do so. However, if the first failure mode is difficult and expensive to fix and eliminate, it would make less sense for the manufacturer to fix it from a purely economical viewpoint.

Although, the above discussion has focused on the benefits of fixing and eliminating the component's first failure mode, it should be noted that the design maturity measure algorithm of the present invention can be employed to determine the benefits of eliminating any particular component failure mode.

To illustrate the benefits of the design maturity measure algorithm, as applied to the second failure mode of the components, consider the previous three hypothetical situations.

In the first hypothetical, component A had a first failure mode at 1 hour, a second failure mode at 2 hours, and a third and final failure mode at 11 hours. This data would be incorporated into the algorithm as follows: $[(11-2)/(2-1))/2]$ or $[(9/1)2]$ or a DM measure of 4.5 (this presupposes that the first failure mode had been previously fixed and eliminated). Note that N=2 in this case because only the l as t two failure modes of the component are used in these calculations. Thus, component A's DM measure percentage of 450% (i.e., $[(4.5)100]$) would represent a 450% increase in component A's life span if the second failure mode is fixed. Compare this to the 500% component life span increase achieved by fixing and eliminating the first failure mode. Clearly, a potential 450% life span increase is highly significant, and accordingly, the manufacturer would probably be inclined to fix and eliminate Component A's second failure mode, in addition to the first failure mode.

In the second hypothetical, component B had a first failure mode at 8 hours, a second failure mode at 8.5 hours, and a third and final failure mode at 9 hours. This data would be incorporated into the algorithm as follows: $[((9-8.5)/(2-1))/8.5]$ or $[(0.5/1)/8.5]$ or a DM measure of 0.06 (this presupposes that the first failure mode had been previously fixed and eliminated). Note that N=2 in this case because only the last two failure modes of the component are used in these calculations. Thus, component B's DM measure percentage of 6% (i.e., $[(0.06)100]$) would represent a 6% increase in component B's life span if the second failure mode is fixed and eliminated. Here, it makes very little economic sense for the manufacturer to fix and eliminate the second failure mode of component B.

In the third hypothetical, component C had a first failure mode at 3 hours, a second failure mode at 4 hours, and a third and final failure mode at 5 hours. This data would be incorporated into the algorithm as follows: $[((5-4)/(2-1))/4]$ or $[(1/1)/4]$ or a DM measure of 0.25 (this presupposes that the first failure mode had been previously fixed and eliminated). Thus, component C's DM measure percentage of 25% (i.e., $[(0.25)100]$) would represent a 25% increase in component C's life span if the second failure mode is fixed and eliminated. This hypothetical is not as clear cut as the first two hypothetical situations; however, if the manufacturer could increase component C's life span by 25% by simply and inexpensively fixing and eliminating the second failure mode, it might appear to make economic sense to do so. However, if the second failure mode is difficult and expensive to fix and eliminate, it would make less sense for the manufacturer to fix it from a purely economical viewpoint.

Figure 9:
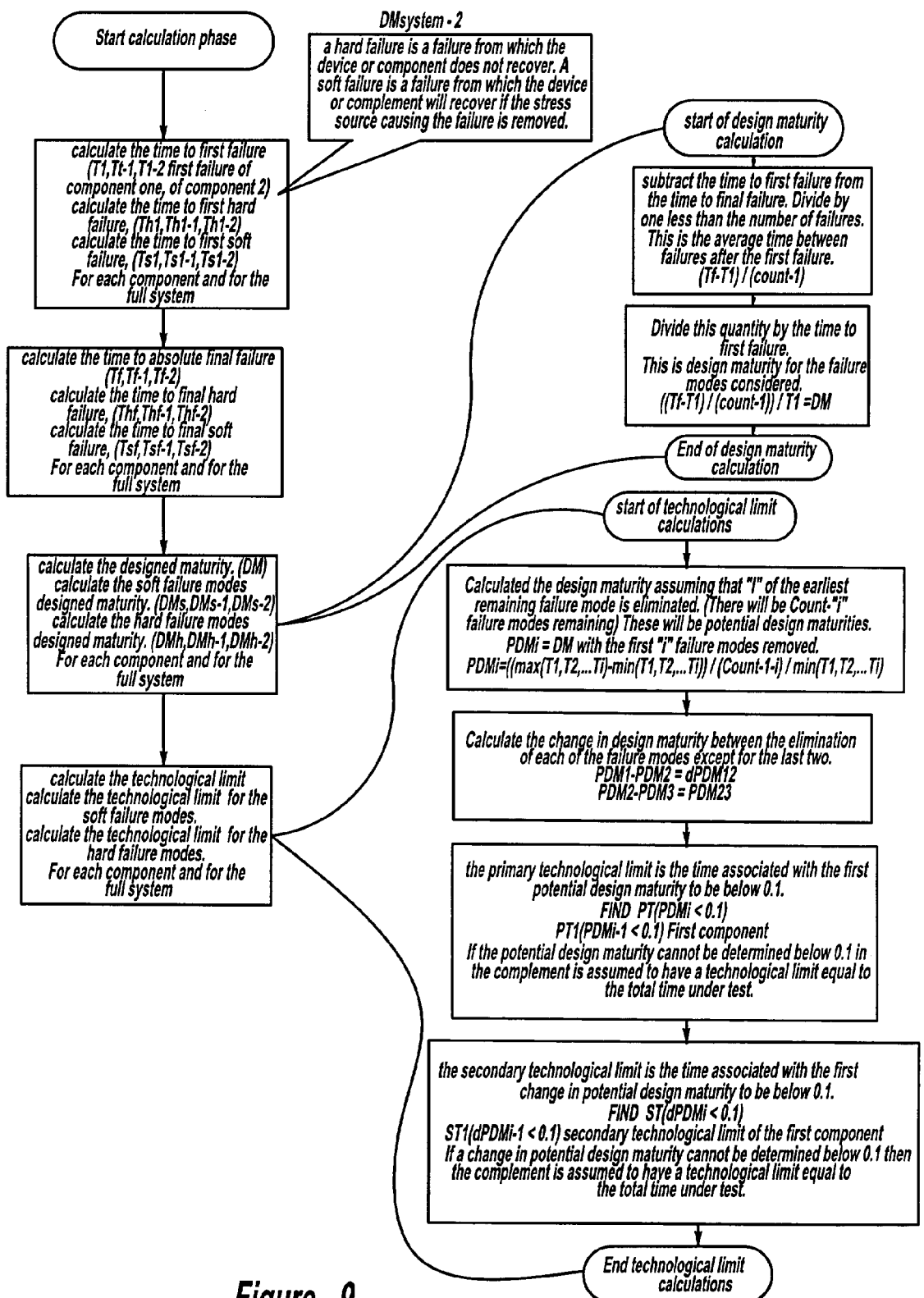
FIG. 9 is a flow chart illustrating the procedures involved in determining design maturity measures and primary and secondary technological limits, in accordance with one aspect of the present invention.

Thus, the usefulness of the design maturity measure algorithm of the present invention is that it enables manufacturers to determine what the benefits of fixing a particular failure mode will be in terms of product or component life span extension. Based on that determination, the manufacturers can then decide whether or not it is economically feasible to fix and eliminate those particular failure modes. For further disclosure of design maturity measure determination procedure see FIG. 9.

The present invention is also useful in determining the technological limits of products and components using design maturity measure data. Technological limits are generally divided into two main groups: primary technological limits and secondary technological limits. Technological limits are generally expressed in terms of time, i.e., minutes, hours, days, and so forth.

A primary technological limit is generally defined as the cumulative time under the stress test procedure below which any failure modes should be fixed and eliminated so that the product's or component's design maturity measure will be below 0.1.

A secondary technological limit is generally defined as the cumulative time under the stress test procedure below which any failure modes should be fixed and eliminated so that the product's or component's potential change in design maturity measure will be below 0.1.

To illustrate these concepts, consider the following hypothetical situation. A product encounters unique failure modes at 1 hour, 4 hours, 5 hours, 6 hours, 10.2 hours, 11.5 hours, and 12 hours during a stress test procedure. Initially, the DM measures of these failure modes must be calculated according to previously described algorithm of the present invention, as follows:

First Failure Mode (1 hour)
$[((12-1)/(7-1)/1]$ or $[(11)/(6)/1]$ or a DM measure of 1.83
Second Failure Mode (4 hours)
$[((12-4)/(7-2)/4]$ or $[(8)/(5)/4]$ or a DM measure of 0.4
Third Failure Mode (5 hours)
$[((12-5)/(7-3)/5]$ or $[(7)/(4)/5]$ or a DM measure of 0.35
Fourth Failure Mode (6 hours)
$[((12-6)/(7-4)/6]$ or $[(6)/(3)/6]$ or a DM measure of 0.33
Fifth Failure Mode (10.2 hours)
$[((12-10.2)/(7-5)/10.2]$ or $[(1.8)/(2)/10.2]$ or a DM measure of 0.09
Sixth Failure Mode (11.5 hours)
$[((12-11.5)/(7-6)/11.5]$ or $[(0.5)/(1)/11.5]$ or a DM measure of 0.04

It should be noted that the DM measure calculations can be done sequentially or randomly with respect to the time that the particular failure modes were encountered.

In order to determine the primary technological limit, the above DM measures are examined to see if any of them fit the criteria of the definition, i.e., the first failure mode having a DM measure of less than 0.1. Both the fifth and sixth failure modes have DM measures less than 0.1. However, the fifth failure mode was the first (i.e., in time) failure mode to occur with a DM measure of less than 0.1, thus, the product's primary technological limit was reached at the time that the fifth failure mode occurred, or put more simply, 10.2 hours.

It should be noted that the same methodology to determine primary technological limits can be applied to individual components of a product, in addition to the product as a whole.

If there were no DM measures of less than 0.1, then the product's primary technological limit would be the total elapsed time during the complete stress test procedure, which in this case was 12 hours.

With respect to determining the secondary technological limit, the change in DM measure is calculated by taking the DM measure of a first failure mode and subtracting from it the DM measure of the next sequential failure mode. In this case the DM measure of the second failure mode would be subtracted from the DM measure of the first failure mode, and so forth, as follows:
First Failure Mode Change in DM Measure
(1.83–0.4) or a change in DM measure of 1.23
Second Failure Mode Change in DM Measure
(0.4–0.35) or a change in DM measure of 0.05
Third Failure Mode Change in DM Measure
(0.35–0.33) or a change in DM measure of 0.02
Fourth Failure Mode Change in DM Measure
(0.33–0.09) or a change in DM measure of 0.24
Fifth Failure Mode Change in DM Measure
(0.09–0.04) or a change in DM measure of 0.05

It should be noted that the change in DM measure calculations can be done sequentially or randomly with respect to the time that the particular failure modes were encountered.

In order to determine the secondary technological limit, the above changes in DM measure are examined to see if any of them fit the criteria of the definition, i.e., the first failure mode having a change in DM measure of less than 0.1. Both the second, third, and fifth failure modes have changes in DM measure of less than 0.1. However, the second failure mode was the first (i.e., in time) failure mode to occur with a change in DM measure of less than 0.1, thus, the product's secondary technological limit was reached at the time that the second failure mode occurred, or put more simply, 4 hours.

If there were no changes in DM measure of less than 0.1, then the product's second technological limit would be the total elapsed time during the complete stress test procedure, which is this case was 12 hours.

It should be noted that the same methodology to determine secondary technological limits can be applied to individual components of a product, in addition to the product as a whole. For further disclosure of primary and secondary technological limit determination procedures see FIG. 9.

The present invention is also useful for determining a system's primary and secondary technological design maturity measure. A system is generally defined as a group of components assembled to perform a function. A component is generally defined as a section of the system which can function independently of the system and is made up of a group of features. A primary technological design maturity measure is generally defined as the design maturity measure of the system based on the primary technological limits. A secondary technological design maturity measure is generally defined as the design maturity measure of the system based on the secondary technological limits.

To illustrate these concepts, consider the following hypothetical situation. A system is comprised of four components, A, B, C, and D. Component A has a primary technological limit of 200 hours and a secondary technological limit of 130 hours. Components B and C both have primary technological limits of 265 hours and secondary technological limits of 265 hours. Component D has a primary technological limit of 240 hours and a secondary technological limit of 135 hours.

The primary technological design maturity measure, or PTDMM, is determined in accordance with the following algorithm:

$$[((PT_{MAX})-(PT_{MIN}))/(N-1))/(PT_{MIN})]=PTDMM$$

wherein $PT_{MAX}$ is the highest primary technological limit of any of the components of the system based on time;
wherein $PT_{MIN}$ is the lowest primary technological limit of any of the components of the system based on time; and
wherein N is the number of components of the system.

The data would be incorporated into the algorithm, as follows: [((265)–(200))/(4–1)/(200)] or [(65)/(3)/(200)] or a primary technological design maturity measure of 0.11. Thus, the system's primary technological design maturity measure percentage would be 11% (i.e., [(0.11)100]).

The secondary technological design maturity measure, or STDMM, is determined in accordance with the following algorithm:

$$[((ST_{MAX})-(ST_{MIN}))/(N-1)/(ST_{MIN})]=STDMM$$

wherein $ST_{MAX}$ is the highest secondary technological limit of any of the components of the system based on time;
wherein $ST_{MIN}$ is the lowest secondary technological limit of any of the components of the system based on time; and
wherein N is the number of components of the system.

Figure 10:
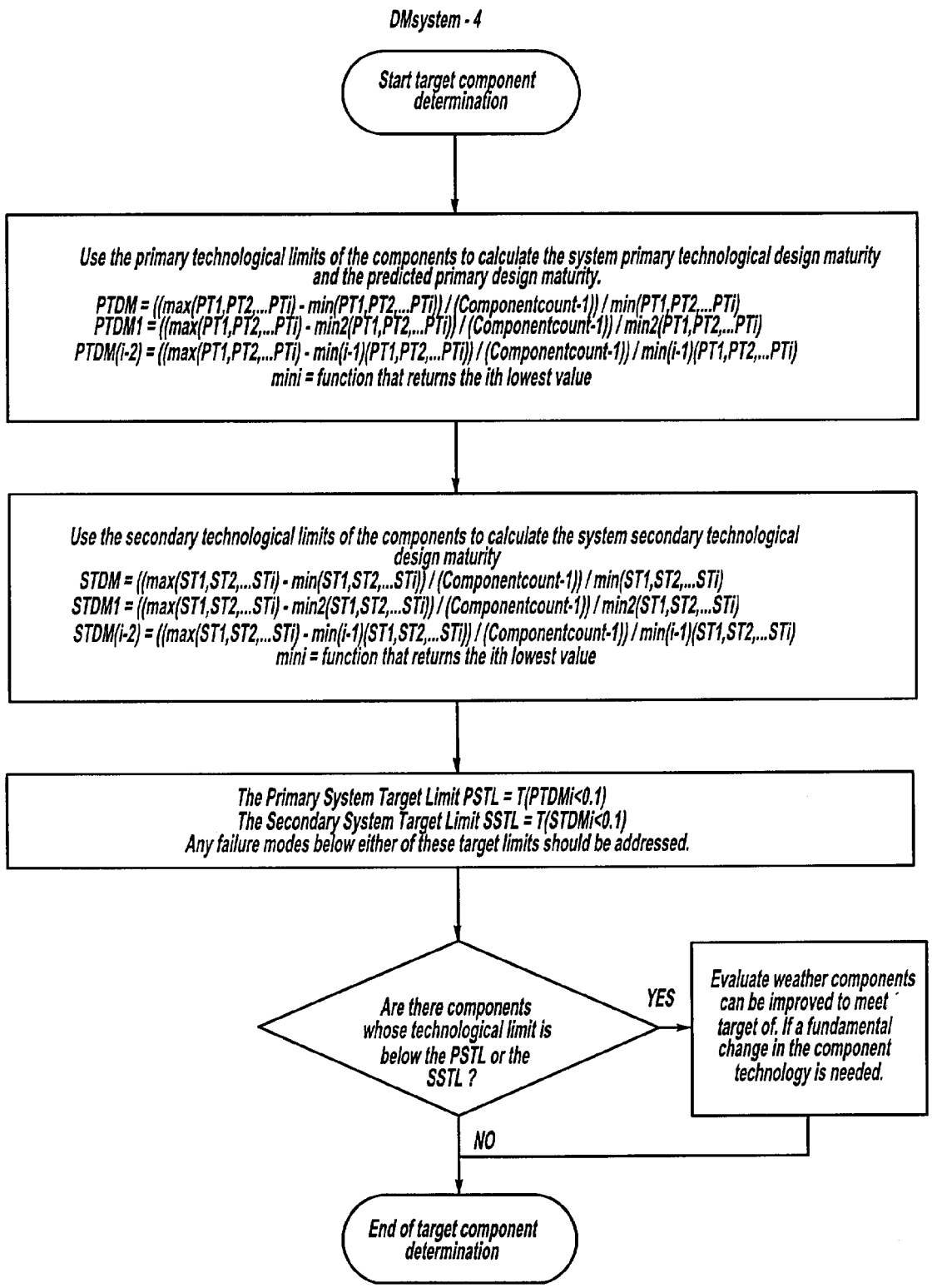
FIG. 10 is a flow chart illustrating the procedures involved in determining system primary and secondary technological design maturity measures and primary and secondary target limits, in accordance with one aspect of the present invention.

The data would be incorporated into the algorithm, as follows: [((265)–(130))/(4–1)/(130)] or [(135)/(3)/(130)] or a primary technological design maturity measure of 0.35. Thus, the system's primary technological design maturity measure percentage would be 35% (i.e., [(0.35)100]). For further disclosure of primary and secondary technological design maturity measure determination procedures see FIG. 10.

The present invention is also useful for determining a system's predicted primary and secondary technological design maturity measures. The predicted primary technological design maturity measure is generally defined as the primary technological design maturity measure if one or more of the minimum primary technological limits of the system's components are fixed and eliminated through replacement or design change. The predicted secondary technological design maturity measure is generally defined as the secondary technological design maturity measure if one or more of the minimum secondary technological limits of the system's components are fixed through replacement or design change.

The predicted primary technological design maturity measure, or PPTDMM, is determined in accordance with the following algorithm:

$$[((PT_{MAX})-(PT_{2MIN}))/(N-1)/(PT_{2MIN})]=PPTDMM$$

wherein $PT_{MAX}$ is the highest primary technological limit of any of the components of the system based on time;
wherein $PT_{2MIN}$ is the penultimate lowest primary technological limit of any of the components of the system based on time; and
wherein N is the number of components of the system.

The data would be incorporated into the algorithm, as follows: [((265)–(240))/(4–1)/(240)] or [(25)/(3)/(240)] or a predicted primary technological design maturity measure of 0.03. Thus, the system's predicted primary technological design maturity measure percentage would be 3% (i.e., [(0.03)100]).

The predicted secondary technological design maturity measure, or PSTDMM, is determined in accordance with the following algorithm:

$$[(ST_{MAX})-(ST_{2MIN}))/(N-1))/ (ST_{2MIN})]=PSTDMM$$

wherein $ST_{MAX}$ is the highest secondary technological limit of any of the components of the system based on time;
wherein $ST_{MIN}$ is the penultimate lowest secondary technological limit of any of the components of the system based on time; and wherein N is the number of components of the system.

The data would be incorporated into the algorithm, as follows: [((265)−(135))/(4−1)/(135)] or [(130)/(3)/(135)] or a predicted primary technological design maturity measure of 0.32. Thus, the system's predicted primary technological design maturity measure percentage would be 32% (i.e., [(0.32)100]).

The present invention is also useful for determining primary and secondary system target limits. A primary system target limit is generally defined as the technological limit of the system based on the primary technological design maturity measure. A secondary system target limit is generally defined as the technological limit of the system based on the secondary technological design maturity measure.

The primary system target limit, or PSTL, is determined by identifying which component's primary technological limit is associated with the first primary technological design maturity measure of less than 0.1. In this case, we have four primary technological limits (i.e., 200, 240, 265, and 265) from which to choose. The lowest primary technological limit of 200 was associated with a design maturity measure of 0.11 (see the above calculation for the primary technological design maturity measure) The penultimate lowest primary technological limit of 240 was associated with a design maturity measure of 0.04 (see the above calculation of the predicted primary technological design maturity measure). Thus, 240 is the primary system target limit.

Figure 11:
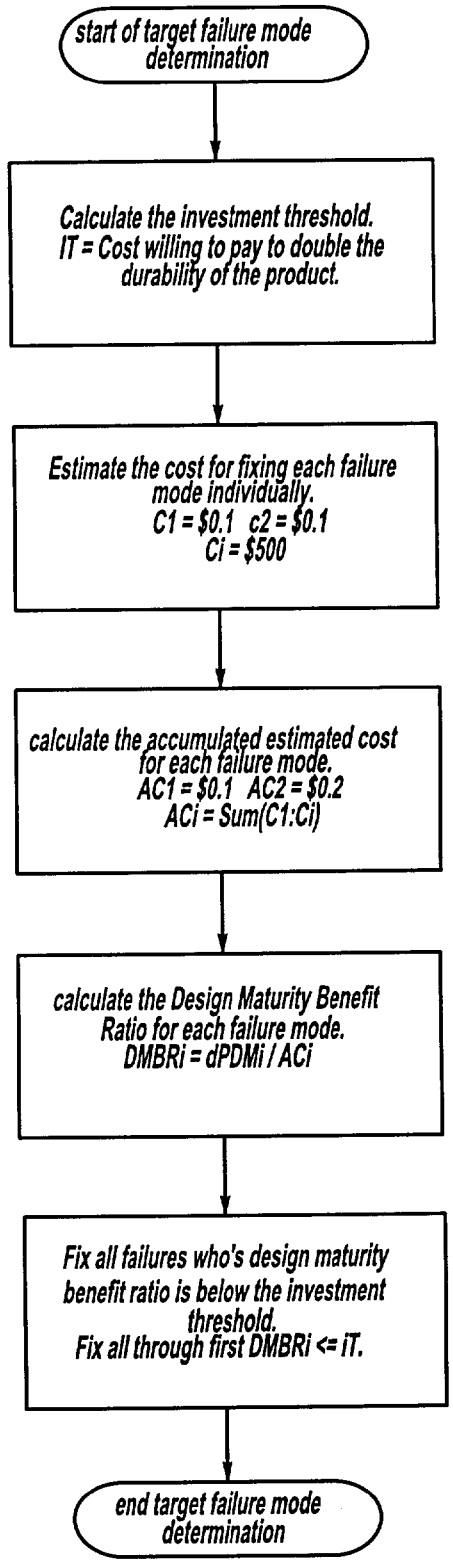
FIG. 11 is a flow chart illustrating the procedures involved in a cost-benefit analysis, in accordance with one aspect of the present invention.
Figure 12:
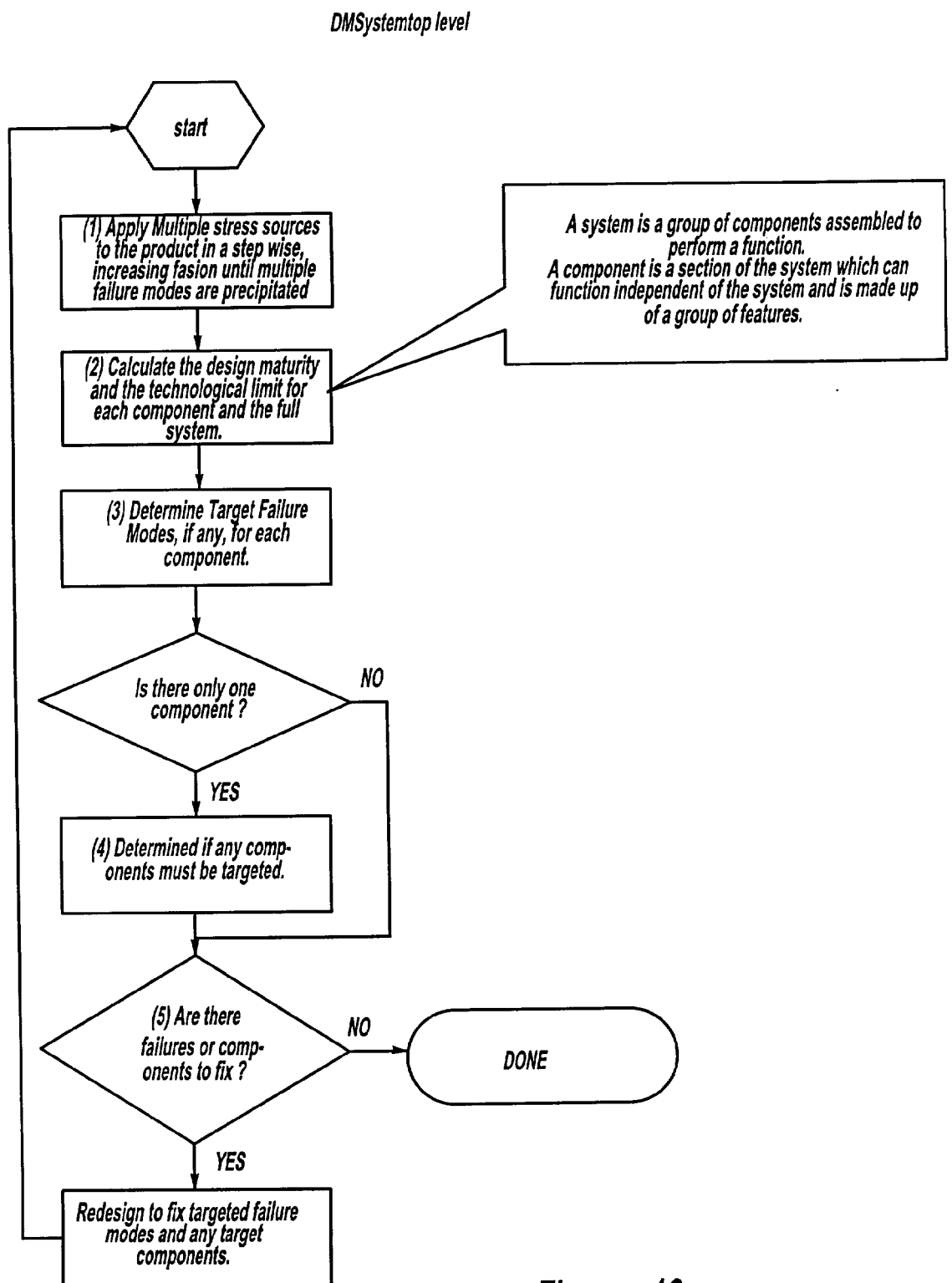
FIG. 12 is a highly simplified flow chart illustrating the procedures involved in stress tests, design maturity measure determination, technological limit determination, target failure mode determination, repairs and redesigns, in accordance with one aspect of the present invention.

The secondary system target limit, or SSTL, is determined by identifying which component's secondary technological limit is associated with the first secondary technological design maturity measure of less than 0.1. In this case, we have four secondary technological limits (i.e., 130, 135, 265, and 265) from which to choose. The lowest secondary technological limit of 130 was associated with a design maturity measure of 0.35 (see the above calculation for the secondary technological design maturity measure). Because 0.35 is greater than 0.1, this particular secondary technological limit can not be the secondary system target limit. The penultimate lowest secondary technological limit of 135 was associated with a design maturity measure of 0.32 (see the above calculation for the predicted secondary technological design maturity measure). Because 0.32 is greater than 0.1, this particular secondary technological limit can not be the secondary system target limit. Thus, the only remaining choice is 265, which is the secondary system target limit. For further disclosure of primary and secondary system target limit determinations see FIGS. 10 and 11.

The foregoing description is considered illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

What is claimed is:

1. An apparatus for applying a force to a product, comprising:
   at least one member for imparting a force, said at least one force imparting member being capable of creating six axis uniform random stresses in the product;
   at least one member for transferring the force from said at least one force imparting member to the product, said at least one force transfer member engaging said at least one force imparting member;
   at least one mounting member for mounting the product thereto, said at least one mounting member engaging said at least one force transfer member; and
   at least one member for allowing said at least one force transfer member to move longitudinally and in all three axes.

2. An apparatus in accordance with claim 1, further comprising:
   a base;
   at least one support member, said at least one support member having first and second ends, said first end of said at least one support member being fastened to said base, said at least one force imparting member being fastened to said at least one support member;
   at least one actuator member for actuating said at least one force imparting member; and
   a planar member, said second ends of said at least one support member being fastened to said planar member, said planar member having an area defining an aperture, said at least one force transfer member extending through the aperture of said planar member.

3. An apparatus in accordance with claim 1, further comprising a first enclosure enclosing said at least one force imparting member.

4. An apparatus in accordance with claim 3, wherein said first enclosure includes an area defining an aperture for receiving said at least one force transfer member.

5. An apparatus in accordance with claim 3, further comprising a second enclosure for enclosing said at least one mounting member.

6. An apparatus in accordance with claim 5, wherein said second enclosure comprises an environmental chamber.

7. An apparatus in accordance with claim 5, wherein said second enclosure includes an area defining an aperture for receiving said at least one force transfer member.

8. An apparatus in accordance with claim 5, further comprising a third enclosure disposed between said first and second enclosures.

9. An apparatus in accordance with claim 1, further comprising:
   a device for subjecting the product to vibration;
   optionally, a device for subjecting the product to a temperature;
   optionally, a device for subjecting the product to pressure;
   optionally, a device for subjecting the product to ultraviolet radiation;
   optionally, a device for subjecting the product to chemical exposure;
   optionally, a device for subjecting the product to humidity;
   optionally, a device for subjecting the product to mechanical cycling; and
   optionally, a device for subjecting the product to mechanical loading.

10. An apparatus in accordance with claim 9, further comprising:
    a device for controlling the amount of vibration that the product is subjected to by the apparatus;
    optionally, a device for controlling the level of temperature that the product is subjected to by the apparatus;
    optionally, a device for controlling the level of pressure that the product is subjected to by the apparatus;
    optionally, a device for controlling the level of ultraviolet radiation that the product is subjected to by the apparatus;
    optionally, a device for controlling the level of chemical exposure that the product is subjected to by the apparatus;

optionally, a device for controlling the level of humidity that the product is subjected to by the apparatus;

optionally, a device for controlling the amount of mechanical cycling that the product is subjected to by the apparatus; and optionally, a device for controlling the amount of mechanical loading that the product is subjected to by the apparatus.

11. An apparatus in accordance with claim 1, wherein said at least one force imparting member comprises a plurality of actuators, said plurality of actuators operating at different frequencies with respect to one another, wherein the difference in frequencies of said plurality of actuators creates a six axis uniform random stress in the product, said plurality of actuators being capable of producing a frequency in the range of about 2 Hz to about infinity.

12. An apparatus in accordance with claim 1, wherein there are three force transfer members.

13. An apparatus in accordance with claim 1, wherein said at least one force transfer member comprises an elongated member.

14. An apparatus in accordance with claim 1, wherein said at least one force transfer member has first and second spaced and opposed ends, said first and second ends having a ball-shaped member extending therefrom.

15. An apparatus in accordance with claim 1, wherein said at least one mounting member has first and second spaced and opposed ends, said first and second ends having an area defining a socket disposed therein.

16. An apparatus in accordance with claim 15, wherein said ball-shaped member engages said socket so at to permit said at least one force transfer member to rotate freely about said at least one mounting member.

17. An apparatus in accordance with claim 1, further comprising at least one hub member engaging said at least one force imparting member and said at least one force transfer member.

18. An apparatus in accordance with claim 17, wherein said at least one hub member includes a surface having an area defining a socket disposed therein.

19. An apparatus in accordance with claim 18, wherein said ball-shaped member engages said socket so at to permit said at least one force transfer member to rotate freely about said at least one hub member.

20. An apparatus in accordance with claim 1, wherein said at least one member for allowing said force transfer member to move longitudinally and in all three axes comprises a gimbal.

21. A method for determining the design maturity measure of a product that has encountered at least first and second unique failure modes during an elapsed time period of a stress test procedure or any portion thereof, comprising:

(a) determining the total number of unique failure modes (N) encountered during the stress test procedure or any portion thereof;

(b) determining the elapsed time period until the first unique failure mode was encountered (Y) during the stress test procedure or any portion thereof;

(c) determining the elapsed time period until the second unique failure mode was encountered (X) during the stress test procedure or any portion thereof; and (d) calculating the design maturity measure in accordance with the formula: $[((X-Y)/(N-1))/Y]$;

wherein X is the elapsed time period until a final unique failure mode was encountered, or any other unique failure mode was encountered other than an initial unique failure mode, during the stress test procedure or any portion thereof;

wherein Y is the elapsed time period until the initial unique failure mode was encountered, or any other unique failure mode was encountered other than the final unique failure mode, during the stress test procedure or any portion thereof; and N is the total number of unique failure modes encountered during the stress test procedure or any portion thereof.

22. The method in accordance with claim 21, further comprising calculating the design maturity measure percentage in accordance with the algorithm: $[(DMM)100]$;

wherein DMM is the design maturity measure.

23. The method in accordance with claim 21, further comprising recording the total number of unique failure modes encountered.

24. The method in accordance with claim 21, further comprising recording the elapsed time until the at least first failure mode was encountered.

25. The method in accordance with claim 21, further comprising recording the elapsed time until the at least second failure mode was encountered.

26. A method for determining the primary technological limit of a product that has encountered at least first and second unique failure modes during an elapsed time period of a stress test procedure, comprising:

determining the design maturity measure in accordance with the formula; $(((X-Y)/(N-1))/Y)$;

wherein X is the elapsed time period until a final unique failure mode was encountered, or any other unique failure mode was encountered other than an initial unique failure mode, during the stress test procedure;

wherein Y is the elapsed time period until the initial unique failure mode was encountered, or any other unique failure mode was encountered other than the final unique failure mode, during the stress test procedure; and N is the total number of unique failure modes encountered during the stress test procedure; and determining if the design maturity measure is less than or greater than 0.1;

wherein the primary technological limit of the product is defined as either the shortest elapsed time period in which a unique failure mode was encountered that had a design maturity measure of less than 0.1, or if there is not a unique failure mode that has a design maturity measure of less than 0.1, then the elapsed time period of the stress test procedure.

27. The method in accordance with claim 26, further comprising identifying the shortest elapsed time period in which a unique failure mode was encountered that had a design maturity measure of less than 0.1.

28. A method for determining the secondary technological limit of a product that has encountered at least first and second unique failure modes during an elapsed time period of a stress test procedure, comprising:

determining the design maturity measure in accordance with the formula: $(((X-Y)/(N-1))/Y)$;

wherein X is the elapsed time period until a final unique failure mode was encountered, or any other unique failure mode was encountered other than an initial unique failure mode, during the stress test procedure;

wherein Y is the elapsed time period until the initial unique failure mode was encountered, or any other unique failure mode was encountered other than the final unique failure mode, during the stress test procedure; and N is the total number of unique failure modes encountered during the stress test procedure; and determining if the design maturity measure change is less than or greater than 0.1 between any two sequential unique failure modes;

wherein the secondary technological limit of the product is defined as either the shortest cumulative time under the stress test procedure in which the difference in design maturity measure between any two sequential unique failure modes is less than 0.1, or if there is not a design maturity measure change of less than 0.1 between any two sequential unique failure modes, then the elapsed time period of the stress test procedure.

29. The method in accordance with claim 28, further comprising identifying the shortest elapsed time period in which a unique failure mode was encountered that had a design maturity measure change of less than 0.1.

30. A method for determining the primary technological design maturity measure of a system having at least two components, wherein the components have at least one primary technological limit, comprising:

determining the highest primary technological limit of any of the components of the system based on time;

determining the lowest primary technological limit of any of the components of the system based on time; and determining the primary technological design maturity measure of the system in accordance with the formula: $[((PT_{MAX})-(PT_{MIN}))/(N-1))/(PT_{MIN})]$;

wherein $PT_{MAX}$ is the highest primary technological limit of any of the components of the system based on time;

wherein $PT_{MIN}$ is the lowest primary technological limit of any of the components of the system based on time; and wherein N is the number of components of the system.

31. A method for determining the secondary technological design maturity measure of a system having at least two components, wherein the components have at least one secondary technological limit, comprising:

determining the highest secondary technological limit of any of the components of the system based on time;

determining the lowest secondary technological limit of any of the components of the system based on time; and determining the secondary technological design maturity measure of the system in accordance with the formula: $[((ST_{MAX})-(ST_{MIN}))/(N-1))/(ST_{MIN})]$;

wherein $ST_{MAX}$ is the highest secondary technological limit of any of the components of the system based on time;

wherein $ST_{MIN}$ is the lowest secondary technological limit of any of the components of the system based on time; and wherein N is the number of components of the system.

32. A method for determining the predicted primary technological design maturity measure of a system having at least two components, wherein the components have at least one primary technological limit, comprising:

determining the highest primary technological limit of any of the components of the system based on time;

determining the penultimate lowest primary technological limit of any of the components of the system based on time; and determining the predicted primary technological design maturity measure of the system in accordance with formula: $[(PT_{MAX})-(PT_{2MIN}))/(N-1))/(PT_{2MIN})]$;

wherein $PT_{MAX}$ is the highest primary technological limit of any of the components of the system based on time;

wherein $PT_{2MIN}$ is the penultimate lowest primary technological limit of any of the components of the system based on time; and wherein N is the number of components of the system.

33. A method for determining the predicted secondary technological design maturity measure of a system having at least two components, wherein the components have at least one secondary technological limit, comprising:

determining the highest secondary technological limit of any of the components of the system based on time;

determining the penultimate lowest secondary technological limit of any of the components of the system based on time; and determining the predicted secondary technological design maturity measure of the system in accordance with formula: $[((ST_{MAX})-(ST_{2MIN}))/(N-1)/(ST_{2MIN})]$;

wherein $ST_{MAX}$ is the highest secondary technological limit of any of the components of the system based on time;

wherein $ST_{2MIN}$ is the penultimate lowest secondary technological limit of any of the components of the system based on time; and wherein N is the number of components of the system.

34. A method for determining the primary system target limit, wherein the system has at least one primary technological limit, the at least one primary technological limit having an elapsed time associated therewith, comprising:

determining which, if any, of the primary technological limits are associated with a design maturity measure of less than 0.1 based on either a primary technological design maturity determination or a predicted primary technological design maturity measure determination;

wherein if there is at least one primary technological limit associated with a design maturity measure of less than 0.1, then the primary technological limit having the shortest elapsed time is the primary system target limit;

wherein if there is no primary technological limit associated with a design maturity measure of less than 0.1, then the primary technological limit having the longest elapsed time is the primary system target limit.

35. A method for determining the secondary system target limit, wherein the system has at least one secondary technological limit, the at least one secondary technological limit having an elapsed time associated therewith, comprising:

determining which, if any, of the secondary technological limits are associated with a design maturity measure of less than 0.1 based on either a secondary technological design maturity determination or a predicted secondary technological design maturity measure determination;

wherein if there is at least one secondary technological limit associated with a design maturity measure of less than 0.1, then the secondary technological limit having the shortest elapsed time is the secondary system target limit;

wherein if there is no secondary technological limit associated with a design maturity measure of less than 0.1, then the secondary technological limit having the longest elapsed time is the secondary system target limit.

* * * * *

UNITED STATES PATENT AND TRADEMARK OFFICE
CERTIFICATE OF CORRECTION

PATENT NO. : 6.247,366 B1
DATED : June 19, 2001
INVENTOR(S) : Porter

It is certified that error appears in the above-identified patent and that said Letters Patent is hereby corrected as shown below:

<u>Title page,</u>
Item [56], References Cited,
U.S. Patent No. 2,850,893 "9/1958" should be -- 4/1956 --.
OTHER PUBLICATIONS, "Pecht, Micheal, et al." reference, "Modelling" should be -- Modeling --.

<u>Column 1,</u>
Lines 8-9, delete "filed Sep. 15, 1997, pending".

<u>Column 12,</u>
Line 41, delete "there" and substitute -- their -- therefore.
Line 60, delete "cut" and substitute -- cup -- therefor.

<u>Column 17,</u>
Line 20, "[(9/1)2]" should be -- [(9/1)/2] --.
Line 22, "I as t" should be -- last --.

<u>Column 20,</u>
Line 13, "(N-1)" should be -- (N-1)) --.
Line 62, "($ST_{MAX}$)" should be -- (($ST_{MAX}$) --.

<u>Column 21,</u>
Line 23, "measure)" should be -- measure). --.

<u>Column 24,</u>
Line 28, "formula;" should be -- formula: --.

<u>Column 25,</u>
Line 67, "[($PT_{MAX}$)" should be -- [(($PT_{MAX}$) --.

UNITED STATES PATENT AND TRADEMARK OFFICE
CERTIFICATE OF CORRECTION

PATENT NO.    : 6,247,366 B1
DATED         : June 19, 2001
INVENTOR(S)   : Porter It is certified that error appears in the above-identified patent and that said Letters Patent is hereby corrected as shown below:

Column 26,
Line 19, "(N-1)" should be -- (N-1)) --.

Signed and Sealed this

Fourth Day of February, 2003

JAMES E. ROGAN
*Director of the United States Patent and Trademark Office*